US009841386B2

(12) United States Patent
Grodzins et al.

(10) Patent No.: US 9,841,386 B2
(45) Date of Patent: Dec. 12, 2017

(54) RADIATION THREAT DETECTION

(71) Applicant: American Science and Engineering, Inc., Billerica, MA (US)

(72) Inventors: Lee Grodzins, Lexington, MA (US); Peter J. Rothschild, Newton, MA (US); William L. Adams, Powell, OH (US)

(73) Assignee: AMERICAN SCIENCE AND ENGINEERING, INC., Billerica, MA (US)

( * ) Notice: Subject to any disclaimer, the term of this patent is extended or adjusted under 35 U.S.C. 154(b) by 846 days.

(21) Appl. No.: 13/650,709

(22) Filed: Oct. 12, 2012

(65) Prior Publication Data
US 2013/0039453 A1 Feb. 14, 2013

Related U.S. Application Data

(60) Division of application No. 12/239,054, filed on Sep. 26, 2008, now Pat. No. 8,325,871, which is a
(Continued)

(51) Int. Cl.
*G01N 23/04* (2006.01)
*G01T 3/06* (2006.01)
*G01V 5/00* (2006.01)

(52) U.S. Cl.
CPC ........... *G01N 23/04* (2013.01); *G01T 3/06* (2013.01); *G01V 5/0025* (2013.01); *G01V 5/0091* (2013.01)

(58) Field of Classification Search
USPC ........................................ 376/153–155, 245
See application file for complete search history.

(56) References Cited

U.S. PATENT DOCUMENTS

| 3,780,291 A | 12/1973 | Stein et al. ................... 250/363 |
| 4,180,737 A | 12/1979 | Kingsley ....................... 250/367 |

(Continued)

FOREIGN PATENT DOCUMENTS

| DE | 40 17 100 A1 | 12/1990 | ............... G01T 1/36 |
| EP | 0 358 965 A1 | 3/1990 | ............... G01V 5/00 |

(Continued)

OTHER PUBLICATIONS

Nittoh et al., "Discriminated neutron and X-ray radiography using multi-color scintillation detector," *Nuclear Instruments and Methods in Physics Research A*, vol. 428, pp. 583-588 (1999).
(Continued)

*Primary Examiner* — Marshall P O'Connor
(74) *Attorney, Agent, or Firm* — Novel IP

(57) ABSTRACT

Systems and methods for detecting clandestine fissile or radioactive material on the basis of emitted radiation and particles (such as neutrons and alpha particles) arising from within the material. Emission by the fissile or radioactive material is detected in conjunction with a conventional x-ray imaging system that includes an external source of illuminating penetrating radiation, at least one detector configured to detect at least the penetrating radiation and to generate a detector signal, and a processor configured as a detector signal discriminator to generate an output indicating whether the detector signal is triggered by an origin other than illuminating penetrating radiation. Active and passive modes of detection are described by some embodiments. Other embodiments are directed toward neutron detection, gamma ray detection with energy resolution, and designs of detectors to enhance the detection of clandestine nuclear material.

7 Claims, 14 Drawing Sheets

Related U.S. Application Data continuation-in-part of application No. 10/750,178, filed on Dec. 31, 2003, now abandoned, which is a continuation-in-part of application No. 09/818,987, filed on Mar. 27, 2001, now abandoned, said application No. 10/750,178 is a continuation-in-part of application No. 10/156,989, filed on May 29, 2002, now abandoned, said application No. 12/239,054 is a continuation-in-part of application No. 10/620,322, filed on Jul. 15, 2003, now abandoned, which is a continuation-in-part of application No. 09/818,987, filed on Mar. 27, 2001, now abandoned, said application No. 10/620,322 is a continuation-in-part of application No. 10/156,989, filed on May 29, 2002, now abandoned.

(60) Provisional application No. 60/192,425, filed on Mar. 28, 2000, provisional application No. 60/360,854, filed on Mar. 1, 2002, provisional application No. 60/192,425, filed on Mar. 28, 2000, provisional application No. 60/360,854, filed on Mar. 1, 2002, provisional application No. 60/396,034, filed on Jul. 15, 2002.

(56) References Cited

U.S. PATENT DOCUMENTS

| | | | |
|---|---|---|---|
| 4,366,382 A | 12/1982 | Kotowski | 378/57 |
| 4,472,822 A | 9/1984 | Swift | 378/10 |
| 4,511,799 A | 4/1985 | Bjorkholm | 250/367 |
| 4,620,099 A | 10/1986 | Schoenig, Jr. et al. | 250/358.1 |
| 4,667,107 A | 5/1987 | Wang | 250/390 |
| 4,795,910 A | 1/1989 | Henderson et al. | 250/483.1 |
| 4,809,312 A | 2/1989 | Annis | 378/146 |
| 5,033,073 A | 7/1991 | Friddell | 378/146 |
| 5,098,640 A | 3/1992 | Gozani et al. | 376/166 |
| 5,179,581 A | 1/1993 | Annis | 378/57 |
| 5,181,234 A | 1/1993 | Smith | 378/87 |
| 5,224,144 A | 6/1993 | Annis | 378/146 |
| 5,253,283 A | 10/1993 | Annis et al. | 378/100 |
| 5,260,982 A | 11/1993 | Fujii et al. | 378/87 |
| 5,334,840 A | 8/1994 | Newacheck et al. | 250/483.1 |
| 5,376,795 A | 12/1994 | Hasegawa et al. | 250/363.04 |
| 5,391,879 A | 2/1995 | Tran et al. | 250/367 |
| 5,420,452 A | 5/1995 | Tran et al. | 257/428 |
| 5,481,584 A | 1/1996 | Tang et al. | 378/98.9 |
| 5,568,499 A | 10/1996 | Lear | 372/45 |
| 5,572,034 A | 11/1996 | Karellas | 250/368 |
| 5,600,700 A | 2/1997 | Krug et al. | 378/57 |
| 5,629,782 A | 5/1997 | Ichimura et al. | 359/9 |
| 5,650,626 A | 7/1997 | Trauernicht et al. | 250/370.09 |
| 5,659,420 A | 8/1997 | Wakai et al. | 359/368 |
| 5,663,944 A | 9/1997 | Mun | 369/121 |
| 5,679,964 A | 10/1997 | Kobayashi et al. | 257/83 |
| 5,734,166 A | 3/1998 | Czirr | 250/390.11 |
| 5,745,265 A | 4/1998 | Hasegawa et al. | 359/15 |
| 5,753,921 A | 5/1998 | Trauernicht et al. | 250/370.09 |
| 5,764,683 A | 6/1998 | Swift et al. | 378/57 |
| 5,838,759 A | 11/1998 | Armistead | 378/57 |
| 5,973,328 A | 10/1999 | Hiller et al. | 250/390.01 |
| 5,978,438 A | 11/1999 | Resnick et al. | 378/4 |
| 6,151,381 A | 11/2000 | Grodzins et al. | 378/90 |
| 6,215,842 B1 | 4/2001 | Resnick et al. | 378/16 |
| 6,262,421 B1 | 7/2001 | Tran | 250/370.09 |
| 6,292,528 B1 | 9/2001 | Wieczorek et al. | 378/19 |
| 6,347,132 B1 * | 2/2002 | Annis | 378/57 |
| 6,370,227 B1 | 4/2002 | Guru et al. | 378/149 |
| 6,507,025 B1 | 1/2003 | Verbinski et al. | 250/358.1 |
| 2002/0067789 A1 | 6/2002 | Wallace et al. | 376/154 |
| 2002/0141529 A1 | 10/2002 | Olsher et al. | 376/245 |

FOREIGN PATENT DOCUMENTS

| | | | | |
|---|---|---|---|---|
| EP | 0 733 928 A2 | 9/1996 | | G02F 1/1335 |
| EP | 0 971 215 A1 | 1/2000 | | G01G 17/02 |
| FR | 2 492 159 A1 | 4/1982 | | G01T 3/06 |
| JP | 7-294653 | 11/1995 | | G01T 1/20 |

OTHER PUBLICATIONS

Novikov, "A method for monitoring of Gd concentration in Gd-loaded scintillators," *Nuclear Instruments and Methods in Physics Research A*, vol. 366, pp. 413-414 (1995).

* cited by examiner

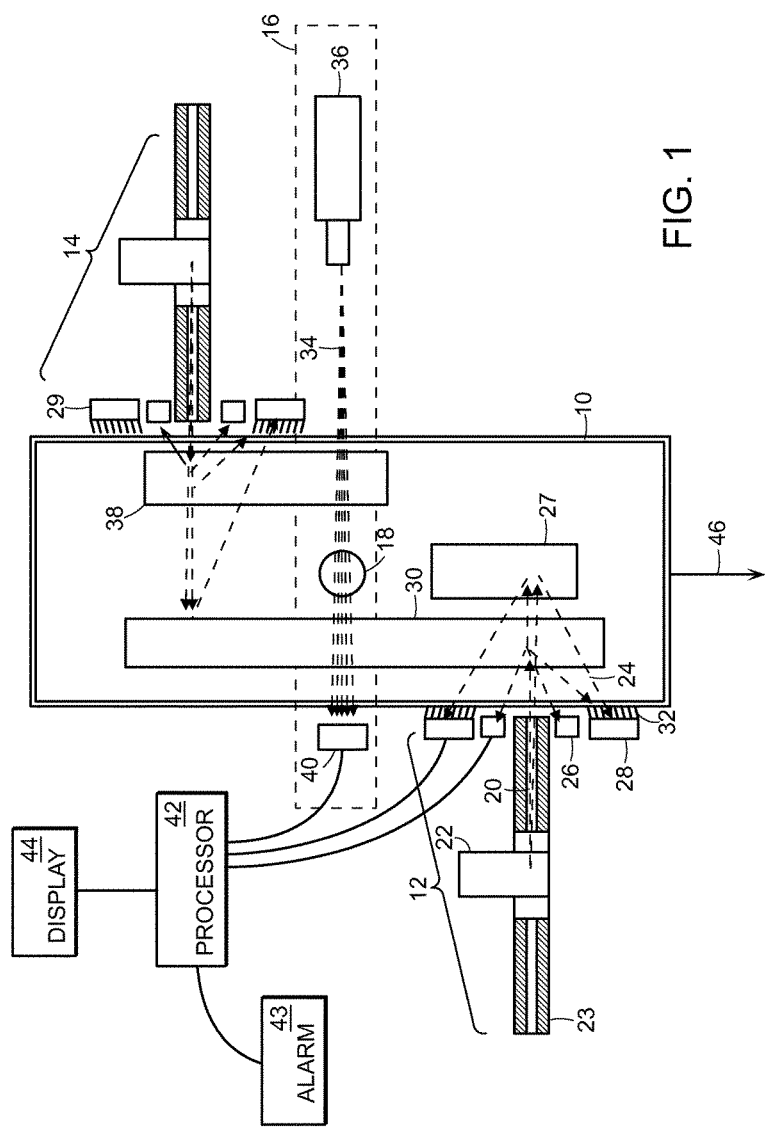

RADIATION THREAT DETECTION

The present application is a divisional application of U.S. patent application Ser. No. 12/239,054, filed Sep. 26, 2008, now allowed, which is a continuation-in-part application of U.S. patent application Ser. No. 10/750,178, filed Dec. 31, 2003, in turn a continuation-in-part of Ser. No. 09/818,987, filed Mar. 27, 2001, which claims priority from a U.S. Provisional Application with Ser. No. 60/192,425, filed Mar. 28, 2000. Co-pending Ser. No. 12/239,054 is also a continuation-in-part application of a U.S. patent application Ser. No. 10/156,989, filed May 29, 2002, which claims priority from a U.S. Provisional Application Ser. No. 60/360,854, filed Mar. 1, 2002.

Co-pending U.S. Ser. No. 12/239,054, of which the present application is a divisional application, is also a continuation-in-part application of U.S. patent application Ser. No. 10/620,322, filed Jul. 15, 2003, which claims priority from U.S. Provisional Application 60/396,034, filed Jul. 14, 2002, and is a continuation-in-part of Ser. No. 09/818,987, filed Mar. 27, 2001, which claims priority from a U.S. Provisional Application with Ser. No. 60/192,425, filed Mar. 28, 2000; and a continuation-in-part application of a U.S. patent application with Ser. No. 10/156,989, filed May 29, 2002, which claims priority from a U.S. Provisional Application with Ser. No. 60/360,854, filed Mar. 1, 2002.

Priority is claimed from all of the aforementioned applications, and all of the aforementioned applications are incorporated by reference herein.

TECHNICAL FIELD

The present invention relates to methods and devices for inspecting containers, or objects contained therein, with penetrating radiation, while, during the course of the same inspection, searching for material with particular signatures (e.g., gamma rays, neutrons, electrons, or alpha particles) that provide an indication that the material might be either fissile or radioactive.

BACKGROUND OF THE INVENTION

Sources of radiation and other nuclear material that might be clandestinely transported across national boundaries must be found. The sources of radiation and clandestine nuclear material may be in the form of "dirty bombs" (e.g., a conventional explosive combined with radioactive nuclides designed to spread radioactive contamination upon detonation), fissile material, and other neutron and radiation emitting sources that may present a hazard to the public. During recent years, the United States government has placed mobile vehicles at strategic areas with gamma ray detectors dedicated to the task of finding fissile material. "Fissile material" includes those radioactive isotopes essential for nuclear explosives, and other isotopes found in conjunction with such radioactive isotopes.

Atomic explosives may be made from $^{235}$U, a rare, naturally occurring, isotope of uranium that lives almost $10^9$ years, or $^{239}$Pu, a reactor-made isotope that lives more than $10^4$ years. $^{235}$U decays with the emission of gamma ray photons (also referred to as 'gammas'), principally at 185.6 keV and 205.3 keV. $^{239}$Pu emits a number of gamma rays when it decays, the principal ones being at 375 keV and 413.7 keV. These gamma rays are unique signatures for the respective isotopes. But fissile material invariably contains other radioactive isotopes besides those essential for nuclear explosives. For example, weapons grade uranium may contain as little as 20% $^{235}$U; the rest of the uranium consists of other isotopes. The other uranium and plutonium isotopes reveal their presence by gamma rays emitted by their daughters. For example, a daughter of $^{238}$U emits a high energy gamma ray at 1,001 keV; a daughter of $^{232}$U, an isotope present in fissile material made in the former USSR, emits a very penetrating gamma ray at 2,614 keV; and a daughter of $^{241}$Pu emits gamma rays of 662.4 keV and 722.5 keV.

It may also be desirable to detect various other radioisotopes, or signatures of such radioisotopes, that may be present in a "dirty bomb". Detecting various isotopes of particular elements, such as cobalt or cesium, may be particularly valuable in attempting to deter terrorist threats.

U.S. Pat. No. 6,347,132, to Annis, describes seeking to detect nuclear weapons materials using an x-ray inspection system. However, Annis teaches that, in order to do so, one processes an x-ray transmission signal based on illuminating x-rays that traverse an inspected object, and, on the basis of characteristics (such as the spatial frequency of features, namely, how diffuse or compact they are) of the transmission image, in conjunction with the absence of scattering of the same illuminating radiation from certain regions, one infers that nuclear materials might be present.

SUMMARY OF THE INVENTION

In one embodiment of the invention, an inspection system for inspecting an object includes an external source of penetrating radiation for generating an illuminating beam and for irradiating the object, at least intermittently, the beam characterized at each instant of time by an instantaneous energy spectrum and an intensity that may be substantially zero during particular (typically periodic) instants of time. The inspection system also has at least one detector configured to detect penetrating radiation including, but not limited to, penetrating radiation from the illuminating beam that is backscattered by the object, and configured to generate a detector signal. Additionally, the inspection system has a processor configured as a detector signal discriminator to receive the detector signal, generate an x-ray image based on the detector signal that depicts at least illuminating radiation backscattered by the object, and also to generate an output that may be perceived by an operator, indicating whether the detector signal is triggered at least in part by an origin other than the penetrating radiation used to illuminate the object. The inspection system has a display showing the x-ray image that depicts at least illuminating radiation backscattered by the object, and has an output that indicates whether the detector signal is triggered at least in part by an origin other than the penetrating radiation used to illuminate the object.

The detector signal discriminator may generate an output based on at least one of source- and detected-signal timing and induced spectral content in the detector signal. The origin may include x-rays, beta rays from that result in the creation of x-rays, and neutrons. The detector may include a segment having selective energy sensitivity. The detector may also include two serial scintillators, one of which may be a heavy fluorescing material such as bismuth, gold, or lead. An x-ray absorbing wall may be interposed between the two serial scintillators. The source of penetrating radiation may be temporally gated by means such as electronic gating or a chopper wheel that may include blocked spokes. The penetrating radiation may take the form of a pencil beam.

In a related embodiment of the invention, the system further includes a current-integrating circuit configured to receive the detector signal of the at least one detector; and a pulse-counting circuit configured to receive the detector signal of the at least one detector, and to operate during a period when the instantaneous energy intensity is substantially zero intermittently.

In another related embodiment of the invention, the at least one detector includes a front scintillator and a back scintillator arranged in series, the detected penetrating radiation traversing the front scintillator before impinging upon the back scintillator, wherein the front scintillator is more sensitive to the detected penetrating radiation below a given threshold than the back scintillator and the back scintillator is more sensitive to the detected penetrating radiation above the given threshold than the front scintillator. The front detector may be more sensitive to x-rays with energy below 100 keV and the back detector may be more sensitive to x-rays with energy above 100 keV. The system may further include a converter configured to convert energy of the detected penetrating radiation before the detected penetrating radiation is detected by the back detector. The converter may be placed adjacent to a side of the back detector that is opposite a side facing the front detector.

Alternative related embodiments of the invention may alter the instantaneous energy spectrum of the source to be capable of exciting characteristic emission lines of fissile elements, examples being uranium and plutonium.

In another alternative related embodiment of the invention, the system further includes a first scintillator capable of detecting neutrons and being less sensitive to gamma-rays and x-rays than neutrons; and a second scintillator capable of detecting photons and being less sensitive to neutrons than gamma rays and x-rays; wherein the detection signal discriminator generates an output when the origin includes neutrons from the object. The first scintillator may be a large area gadox screen, a $^6$Li-based scintillation screen, or a high pressure $^3$He proportional counter. The second scintillator may be essentially transparent to neutrons, with the first and second scintillators serially arranged such that detected neutrons traverse the second scintillator before impinging on the first scintillator. Alternatively, the second scintillator may be a moderator of fast neutrons and may capture high energy photons, with the first and second scintillators serially arranged such that detected neutrons traverse the second scintillator before impinging on the first scintillator. In such an instance the second scintillator may be a plastic or liquid scintillator; the thickness of the scintillator may be in the range of approximately 2 cm. to 10 cm, and may be segmented.

In another embodiment of the invention, a directional detector of radioactive emissions includes a scintillator for capturing an emission from a radioactive source, the scintillator having a detection dimension with a total thickness greater than the mean free path of the emission in the scintillator; and an optical detector configured to detect photons emitted from the scintillator in a direction of the detection dimension. The scintillator may emit photons after capturing neutrons, the neutron mean free path in the scintillator being shorter than the photons mean free path in the scintillator. As well, the scintillator may include at least two separate pieces separated by the optical detector, the optical detector being substantially neutron transparent. The directional detector may further include shielding configured to prevent the scintillator from capturing neutrons directed from a direction other than the direction of detection dimension. The shielding may substantially include at least one of $^6$Li, $^{10}$B, $^{113}$Cd, and $^{157}$Gd. The directional detector may also include another optical detector positioned on an opposite side of the scintillator from the optical detector. The directional detector may further include a neutron moderator material surrounding at least a portion of the scintillator. The neutron moderator may contain hydrogen, and may be made of high density polyethylene or water.

In an alternate embodiment of the invention, a method for detecting neutrons includes providing a scintillator containing high neutron-capture-cross-section atoms for capturing the neutrons and emitting electromagnetic radiation, at least one dimension of the scintillator exceeding the mean free path in the scintillator of a photon of a specified wavelength range; and detecting photons at the specified wavelength range with a photodetector characterized by a position with respect to the scintillator. The method may include the step of inferring a direction of a detected neutron with the position of the photodetector, and may further include the step of moderating incident fast neutrons for capture by the containing high neutron-capture-cross-section atoms.

In another alternate embodiment of the invention, a method for detecting concealed fissile material includes providing a first scintillator screen for absorbing massive fission products and generating visible light; a second scintillator screen in a path of photons that have traversed the first scintillator screen; a heavy element backing in a path of photons that have traversed the second scintillator screen for generating Auger electrons and concomitant secondary photons; and detecting visible photons arising in the first and second scintillators.

Another alternate embodiment of the invention is directed toward a method for creating an x-ray image of an object and detecting clandestine nuclear material associated with the object. The method includes the steps of illuminating the object with penetrating radiation; detecting emission, including penetrating radiation, emanating from the object; producing an x-ray image of the object based on the detected emission; and distinguishing between detected emission due to scattered penetrating radiation with the object and detected emission due to the clandestine nuclear material. The step of distinguishing may include distinguishing detected emission due to fissile material or a dirty bomb. The detected emission may include gamma rays, x-rays generated by beta rays, or neutrons from the clandestine nuclear material. The step of illuminating the object may also include at least one of moving the object relative to a neutron detector and moving the neutron detector relative to the object, and further include the step of correlating a detection signal from the neutron detector with the relative position of the neutron detector and the object to identify the approximate location of a neutron emitter. The method may further include locating the clandestine nuclear material associated with the object using the x-ray image. The method may also include the steps of identifying a potential location of the clandestine nuclear material using the x-ray image; and redetecting emission emanating from the object after repositioning the object based on the identified potential location. The step of illuminating the object may also include illuminating the object intermittently, and the step of distinguishing may include distinguishing based on at least the source- and detected-signal timing. The step of distinguishing may also include distinguishing based on at least a distribution of photon energies of the detected emission. The step of detecting emission may include detecting emission due to x-ray fluorescence induced by interaction of the penetrating radiation with the clandestine nuclear material.

Another method associated with an embodiment of the invention is directed towards creating an x-ray image of an object and detecting clandestine nuclear material associated with the object. The method includes illuminating the object with penetrating radiation; detecting emission, including penetrating radiation, emanating from the object; producing an x-ray image of the object based on the detected emission; and identifying heavy metal shielding (e.g., tungsten or lead) of clandestine nuclear material associated with the object based on at least identifying a characteristic emission line of active x-ray fluorescence produced by an interaction between the heavy metal shielding and the penetrating radiation. The heavy metal shielding may also be identified at least in part by a distribution of photon energies of the detected emission.

In accordance with another aspect of the present invention, an inspection system is provided for inspecting an object. The system has a bed moveable along a first direction having a horizontal component and a source of penetrating radiation coupled to move with the bed. The source, in turn, includes an intermittent beam transmitter of a kind blocking a penetrating radiation beam during a specified portion of each period of recurrent periods of substantially constant duration, the beam comprised of photons generated by the source of penetrating radiation for irradiating the object. The system has a detector module coupled such that the detector module moves in coordination with the bed. The detector module has a scintillator sensitive to photons of the penetrating radiation beam and a detector sensitive to particles having mass that are emitted by fissile and radioactive material. The system, finally, has a radioactive-source-identifying detection circuit including an off-period discriminator particularly adapted, by virtue of the off-period discriminator, to distinguish particles detected by the detector module during the specified portion of each period during which the penetrating radiation beam is blocked.

In alternate embodiments of the invention, the manifestation of the capture of neutrons may be the emission of electromagnetic radiation. A second detector may be provided that includes an optical detector for detecting the emitted electromagnetic radiation and generating an electrical signal. The detector module may include a segment having selective energy sensitivity with respect to photons of the penetrating radiation beam and electromagnetic radiation emitted by atoms of the detector, and the detector module may also have at least one of a current-integrating circuit and a pulse counter.

The detector module may have two serial scintillators, and an x-ray absorbing wall may be interposed between the two serial scintillators.

In accordance with yet another aspect of the invention, a method is provided for inspecting a container. The method has steps of:

a. illuminating the container with a beam of penetrating radiation comprised of photons from a source coupled to a mobile platform;

b. detecting penetrating radiation emanating from the container; and c. distinguishing between detected radiation due to scatter of photons from the beam of penetrating radiation and detected radiation due to emission by fissile and radioactive material on a basis of the detected radiation due to scatter of photons from the beam being of lower energy per photon than the detected radiation due to emission by fissile and radioactive material.

A further step may include activating an alarm upon detection of emission by fissile and radioactive material.

BRIEF DESCRIPTION OF THE DRAWINGS

The foregoing features of the invention will be more readily understood by reference to the following detailed description taken with the accompanying drawings:

FIG. 1 provides a top view of a cargo container being examined by two backscatter x-rays systems, one on either side of the container, and two orthogonal transmission systems, one horizontal, the other vertical, as an example of an inspection system that may be employed also for detection of fissile and radioactive material in accordance with a preferred embodiment of the present invention;

DETAILED DESCRIPTION OF PREFERRED EMBODIMENTS

Figure 2A:
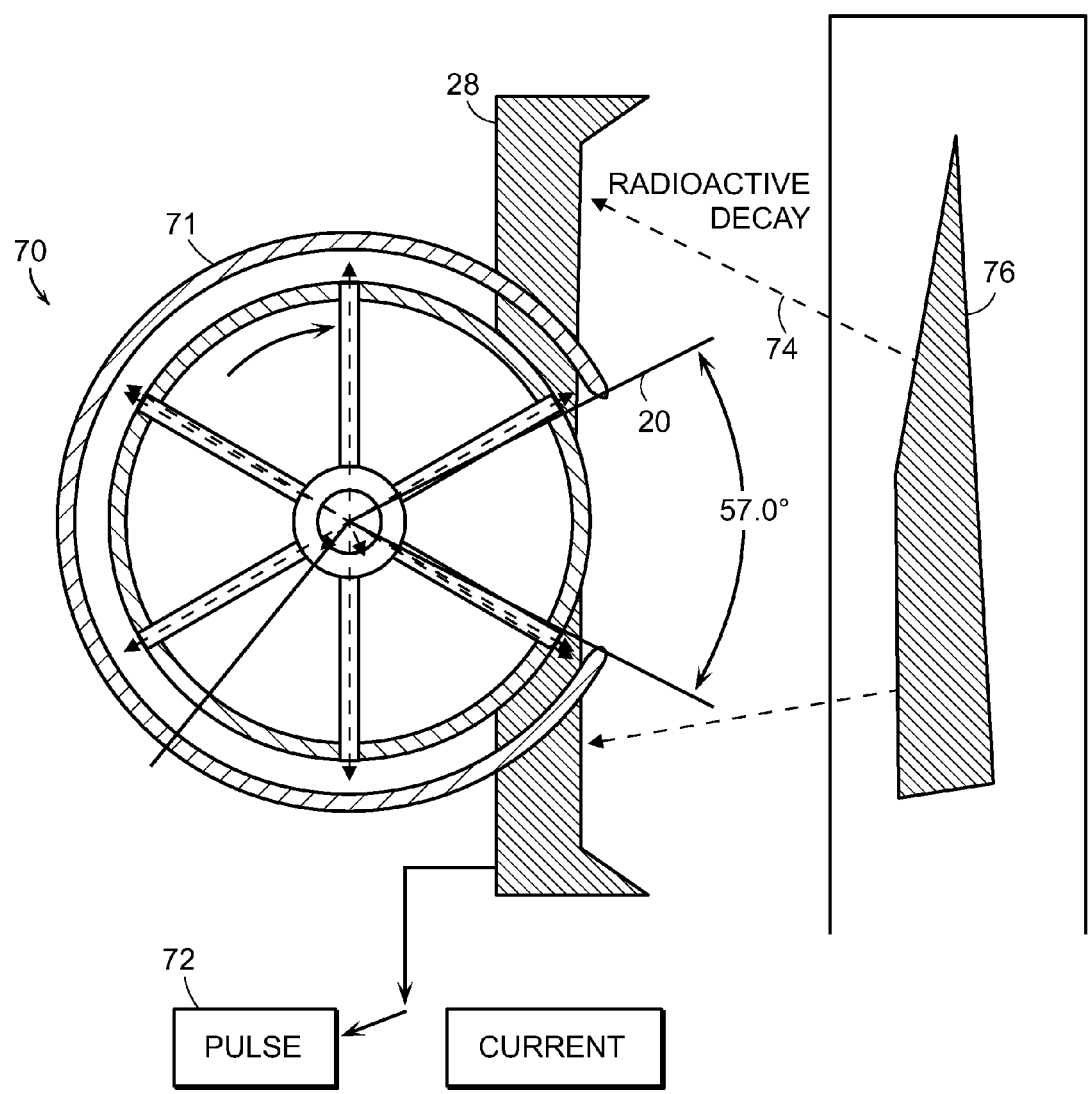
FIG. 2A depicts a passive method for detecting ionizing radiation emitted from the target object, in accordance with an embodiment of the invention, wherein, when no x-ray beam is present in the inspection tunnel or when the x-ray beam is present and the counting rate is low enough, the detector is switched to pulse mode.

Embodiments of the invention are directed toward methods and devices for detecting clandestine nuclear material such as sources of radiation, neutrons, and other particles (e.g., alpha particles). Whereas prior inspection systems are based on detecting radiation either transmitted through an inspected object or scattered by the object, the present invention additionally makes use of radiation that arises solely from within the inspected object.

Some embodiments of the present invention are directed toward ways in which x-ray inspection systems, currently in use for detection of contraband materials such as drugs and conventional weapons and conventional explosives, may additionally be used for finding fissionable or radioactive material associated with scanned objects or in the containers they examine. Airport installations typically employ lower energy (<250 keV) x-ray systems, while high energy (>450 keV) x-ray systems are becoming common at border crossings. Some techniques are passive; i.e., the gamma rays from the clandestine nuclear materials are the signatures for an alert. Several ways of carrying out such passive measurements are described.

Other methods, in accordance with the present invention, are active; i.e., the x-rays that illuminate a container excite fluorescence of a material and the characteristic emission is detected. These methods may involve exciting the atoms of high atomic number materials such as uranium, plutonium, or lead, with a beam of x-rays, and looking for the fluorescence x-rays as the atoms return to their initial unexcited ground state. For example, a beam of x-rays with an endpoint energy of 225 keV can be used to excite uranium atoms, which then emit signature fluorescence x-rays with energies of 94 keV to 111 keV. Photons that are detected from either the passive or active modes may be the result of Bremsstrahlung radiation (i.e., photon emission from a material after beta particle interaction). Other embodiments of the invention are directed toward designs of detectors that may be utilized to enhance the ability to distinguish, or simultaneously, detect neutrons and radiation that are indicative of the presence of fissile material or other radiation sources such as dirty bombs.

Detection of Clandestine Nuclear Material

Some embodiments of the invention make use of systems in which a beam of x-rays is swept through a plane of a container. X-rays transmitted through the container are detected in transmission detectors while x-ray backscattered from the container and its contents are detected in large area backscatter detectors. In the discussion that follows, illustrative calculations make use only of the backscatter detectors.

Inspection systems that may be used for practice of the present invention are of the variety described and shown in U.S. Pat. No. 6,151,381, which is herein incorporated by reference. Other inspection systems that may be used for practice of the present invention are of particular utility for the inspection of large cargo containers such as trucks or sea/air containers in that they employ mobile platforms that may be driven past the inspected container during the course of the inspection. Such systems are described in U.S. Pat. No. 5,764,683, which is incorporated herein by reference.

Referring now to FIG. 1, a top view is shown of a cargo container 10 being examined by two backscatter x-ray systems 12 and 14, one on either side of container 10, and two orthogonal transmission systems, one horizontal 16, the other vertical 18. These inspection systems are shown by way of example, and single inspection systems or different combinations of systems may be used within the scope of the present invention. One or more generators of penetrating radiation may be used for each of the transmission and scatter modalities.

Describing, first, backscatter x-ray systems 12 and 14, x-ray beam 20 is emitted by an x-ray source 22 of one of various sorts known to persons skilled in the art. Beam 20 may also be comprised of other forms of penetrating radiation and may be monoenergetic or multienergetic, or, additionally, of varying spectral characteristics. Backscatter x-ray beam 20 is typically generated by a DC voltage applied to the anode of an x-ray tube 22 so that beam 20 is typically continuous. However, a beam 20 of other temporal characteristics is within the scope of the invention. Beam 20 has a prescribed cross sectional profile, typically that of a flying spot or pencil beam and is scanned in time, as by chopper wheel 23, or another spatial modulator, thereby creating an overall profile varying in time. The beam 20 may also have other geometrical configurations, such as a fan beam. Beam 20 will be referred to in the present description, without limitation, as an x-ray beam.

Various means are known in the art for mechanically or electronically sweeping a beam of penetrating radiation, including, for example, the rotating chopper wheel 23 depicted in FIG. 1 or electronic scanning is described in detail, for example, in U.S. Pat. No. 6,421,420, issued Jul. 16, 2002, which is incorporated herein by reference.

Penetrating radiation scattered by an object 27 within enclosure 10 is detected by one or more x-ray detectors 26 and 28. X-ray detectors 28 may be disposed at varying distances from x-ray beam 20 for differential sensitivity to near-field objects 30 and far-field objects 27, as described, for example, in U.S. Pat. No. 6,151,381. In order to obtain greater spatial resolution of the source of scattered radiation, collimators 32 may be employed, as known to persons skilled in the x-ray art, for narrowing the field of view of segments of detector 28.

Transmission system 16 employs an x-ray beam 34 produced by source 36 which is typically a high energy source of penetrating radiation such as a linear accelerator (Linac) for example. X-ray emission from a linear accelerator is inherently pulsed, with typical pulse rates in the range between 100 and 400 pulses per second. The portion of transmission beam 34 which traverses enclosure 10 and objects 30 and 38 contained within the enclosure is detected by transmission detector 40.

The electrical output signals produced by detectors 26, 28, and 40 are processed by processor 42 to derive characteristics such as the geometry, position, density, mass, and effective atomic number of the contents from the scatter signals and transmission signals using algorithms known to persons skilled in the art of x-ray inspection. In particular, images of the contents of enclosure 10 may be produced by an image generator. As used in this description and in the appended claims, the term "image" refers to an ordered representation of detector signals corresponding to spatial positions. For example, the image may be an array of values within an electronic memory, or, alternatively, a visual image may be formed on a display device 44 such as a video screen or printer. The use of algorithms, as known in the art of x-ray inspection, for identifying suspect regions within the enclosure, and identification of the presence of a specified condition by means of an alarm or otherwise, is within the scope of the present invention. When so specified, an image uses the backscattered radiation as a key to the spatial distribution of the scattering material.

In many applications, it is desirable that enclosure 10 be inspected in a single pass of the enclosure through the x-ray inspection system. Enclosure 10 may move through the system in a direction indicated by arrow 46, either by means of self-propulsion or by any means of mechanical conveyance of the enclosure with respect to the system. Alternatively, the enclosure 10 may not move while an arrangement of detectors and source of penetrating radiation may be rotated and/or translated with respect to the enclosure 10 to provide an x-ray scan of the enclosure 10. Detectors 26, 28, and 40, used in systems for inspection of the contents of baggage or cargo containers are typically operated in a current integration mode rather than in a mode of counting individual x-ray pulses by virtue of count rates that are typically too high to permit counting and processing individual x-ray pulses. Images of the distributions in the currents produced by the transmitted and backscattered x-rays are typically built up as the container passes through the plane of x-rays.

Figure 2B:
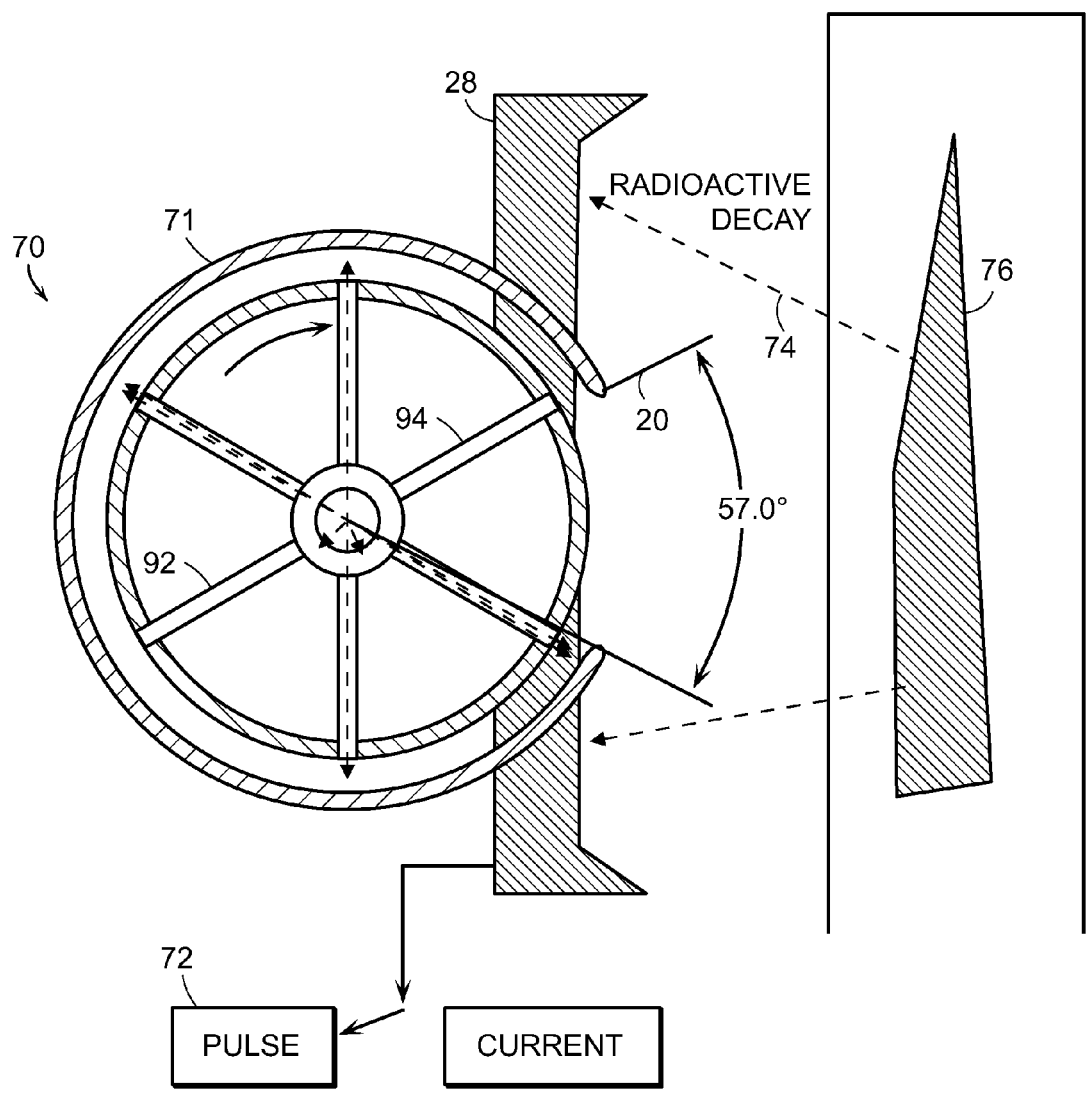
FIG. 2B depicts a passive method for finding ionizing radiation emitted from the target object, in accordance with an embodiment of the invention, wherein at least one of the spokes of the pencil beam forming wheel is filled with x-ray absorbing material so that no radiation from the x-ray source is sent into the target volume and the detector, switched to the pulse mode, is sensitive only to ambient radiation and radiation emitted from the target volume.

Some embodiments of the invention may configure a processor to act as a detector signal discriminator in an x-ray system exemplified by features depicted in FIG. 1; these x-ray systems may allow x-ray imaging systems, as known to those skilled in the art, to operate in conjunction with the detector signal discriminator. The detector signal discriminator is configured to receive a detector signal from the system, and to generate an output indicating whether the detector signal is triggered at least in part by an origin other than the penetrating radiation backscattered by an object being scanned, or other than by any penetrating radiation used to illuminate the object. Processor 42 may operate as a detector signal discriminator, for example, by identifying the presence of detected signal during a portion of time when no illuminating radiation is incident on the object. FIG. 2B shows such an instant of time. Any signal detected by detector 28 during the instant of time when the illuminating beam is blocked must be triggered by an origin other than the penetrating radiation used to illuminate the object.

Since beam 20 (shown in FIG. 4) is blocked by cowling 71 during identical portions of each revolution of chopper wheel 70, synchronous detection of signal during the blocked intervals acts as a radioactive-source-identifying detection circuit including an off-period discriminator particularly adapted, by virtue of the off-period discriminator, to distinguish particles detected by the detector module during the specified portion of each period during which the penetrating radiation beam is blocked.

The detector signal may be triggered by the detection of neutrons or penetrating radiation (e.g., x-rays and gamma rays). The output may be based at least on one of source- and detected-signal timing and induced spectral content in the detector signal. Other embodiments of the invention are directed to related and corresponding methods that implement a detector signal discriminator as described above. The details of source- and detected-signal timing and induced spectral content in the detector signal are discussed herein in terms of passive and active methods for discriminating radiation emanating from the inspected object as opposed to radiation derived from the illuminating beam, either directly or by scattering by atoms of the object.

Though some methods described herein refer to the specific detection of uranium or plutonium, it is readily understood by those skilled in the art that the methods may be employed to detect other radioactive materials. For example, $^{137}Cs$, a commonly available radioactive isotope that could be used by terrorists, emits a signature gamma ray at an energy of 662 keV. Another common isotope is $^{60}Co$ that emits gamma rays of 1173 keV and 1332 keV. These gamma rays can be detected passively, may be indicative of the isotopes and the possible presence of a dirty bomb used by terrorists.

It is also to be understood that features of the invention need not be represented in all figures depicting various embodiments; thus, for example, while processor 42 is depicted with respect to the system shown in FIG. 1, it is not to be inferred that processor 42 may not equally well be used in conjunction with components shown in all of the other drawings.

Passive Method I. Gated Detectors:

In some embodiments of the invention, discrimination of a detector signal is achieved by utilizing source- and detected-signal timing. Referring to FIGS. 2A and 2B, the x-ray beams 20 in x-ray inspection systems typically sweep, as by rotation of chopper wheel 70, through the inspection volume during a large fraction of the operating time. During the remaining fraction of each sweep cycle there are essentially no source x-rays striking the target container. Thus, during the time of source quiescence, the detectors are only counting background. Alternatively, one or more apertures of the chopper wheel 92, 94 may be removed or blocked, as shown in FIG. 2B, by a material that is opaque to a range of x-ray energies, thus increasing the period in which detectors may be counting photons while an object is not illuminated by an x-ray beam. Such a material constitutes the cross-hatched cowling 71 shown in FIGS. 2A, 2B, 3, and 4. Thus an increase in sensitivity and efficiency may be achieved while searching the target volume. Other mechanical devices may be substituted to create x-ray beams in a manner that provides a time of source quiescence.

In another alternative, a beam that is produced by an x-ray system may be gated electronically (i.e. turned on and off electronically) to allow background measurements. Electronic gating of the pencil beam, for example by the use of a gating grid in the x-ray generator, is a preferred method that gives flexibility to the procedure and obviates the need to add shielding material. This alternative may have advantages over mechanically blocking the beam that include having less x-ray leakage during the source quiescence time, and faster on/off times.

In the geometry of FIG. 2A, a beam 20 is directed into the target area for about 95% of the time. Thus, a target container is being inspected by the x-ray beam 20 for 95% of the time it is in the target chamber, leaving only 5% of the time for counting radioactivity without a beam striking the container. The "quiescent-time" is typically only 0.2 seconds (5% of 4 seconds of inspection per bag) but may still be capable of finding clandestine radioactivity as the following example shows.

The 185.6 keV gamma rays are emitted in 53% of the decays of $^{235}U$ (shown as object 76) but only a thin layer of the bulk uranium is accessible since the mean free path of 185.6 keV gammas in uranium is only 0.36 mm. Still, every square centimeter of 10% enriched uranium will emit ~two thousand 185.6 keV gamma photons per second, giving rise to a count of 2,000×0.004=8 counts for every square centimeter of surface area of uranium that faces the detectors. A 1" cube of uranium (weighing ~¾ pounds) would signal its presence with ~50 counts in the 0.2 second off-period of the inspection. A signal of this magnitude is easily discriminated.

The signal from clandestine radioactivity relative to the background noise can be enhanced substantially in a number of ways including increasing the off-time of the sweeping x-ray beam as shown in FIG. 2B, improving the detection efficiency, increasing the solid angle of detection, and lowering the noise level at the gamma ray energies of interest.

In a preferred embodiment, particularly useful for lower energy (140 keV-200 keV) x-ray systems, the noise level at the gamma ray energies of interest can be substantially reduced by switching the output from backscatter detectors 28 to a pulse counting circuit 72 during the fraction of the operating cycle during which the source of x-ray irradiation is off. During this period, individual 185.6 keV gamma rays 74 can be detected and analyzed with low noise levels at that energy. Pulse counting circuit 72 may be used in conjunction with other embodiments of the invention other than that depicted in FIG. 2B, and constitutes a particularized feature of the detector circuitry that allows processor 42 (shown in FIG. 1) to discriminate between detections made when the source of x-ray irradiation is not providing an illuminating beam incident on the inspected object.

In another preferred embodiment, the pulse-counting mode is utilized whenever the count rate in the backscatter detectors falls below a predetermined value, for example 100,000 counts/sec, whether or not the x-ray beam is being sent into the target chamber. The predetermined maximum count rate is chosen as that rate at which it is still practical to measure the energy of the individual photons. When the energy of individual photons detected in backscatter detectors can be analyzed then it becomes practical to search for the 185.6 keV gamma rays from $^{235}$U even while imaging the luggage. The reason is that the energies of the Compton backscatter x-rays, produced by the incident x-ray beam 20, are always lower in energy that 185.6 keV and therefore do not interfere. Specifically, the maximum backscattered Compton energies for x-ray beams produced by electron beams of 160 keV, 220 keV and 440 keV (the maximum energy used in any commercial backscatter system) are 104 keV, 127 keV and 178 keV. A luggage security system such as shown in FIG. 1 may, therefore, advantageously continue to operate normally while the fissile detection system operates efficiently in the background, as described.

In another preferred embodiment, one or more of the spokes are solid rather than hollow. FIG. 2B shows two, diametrically opposite spokes 92, 94 that are blocked. In that example, the beam is restricted from the target chamber for slightly more than a third of the time, or about 1.3 seconds. The backscatter detectors operate for about 1.3 seconds as detectors of radioactive material in a piece of luggage, free from radiation correlated with the x-ray beam 20; a gain in sensitivity of more than a factor of six.

In still another preferred embodiment, a backscatter detector configuration is proposed that operates in the current mode, as opposed to the pulse counting mode, and specifically looks for the 185.6 keV radiation while luggage is being examined with the radiations from the x-ray beam.
Passive Method II. Continuous Detection:

Several modes are described to search, during the imaging time, for the radioactive emission of the 185.6 keV gamma ray from $^{235}$U, and other emissions in the range from approximately 100 keV to 200 keV. Some modes utilize the fact that the maximum energy of the Compton backscattered x-rays that form the x-ray backscattered image is less than the sought for 185.6 keV gamma ray.

The minimum energy of the gamma rays from fissile material is 187 keV. The maximum energy of x-rays detected in the backscatter counters is given by:

$$E^{scattered} = \frac{E^{incident}}{\left(1 + \frac{E^{incident}(1 - \cos\theta)}{m_e c^2}\right)},$$

where $E^{incident}$ is the energy of an incident photon, $E^{scattered}$ is the maximum energy of a scattered photon, $m_e c^2$ is the rest energy of an electron, and 2 is the scattering angle. In the backward direction, $E^{scattered}$ is typically only 100 keV for 160 keV x-ray generators and 170 keV for 450 keV generators. The preponderance of detected x-rays, thus, in either passive or active inspection modality, have energies well below 100 keV. It is therefore feasible to count continuously (that is, during the inspection itself) with a detector that has a threshold at say 160 keV, a straightforward task if the radiation is detected with a pulse counter.

Figure 3:
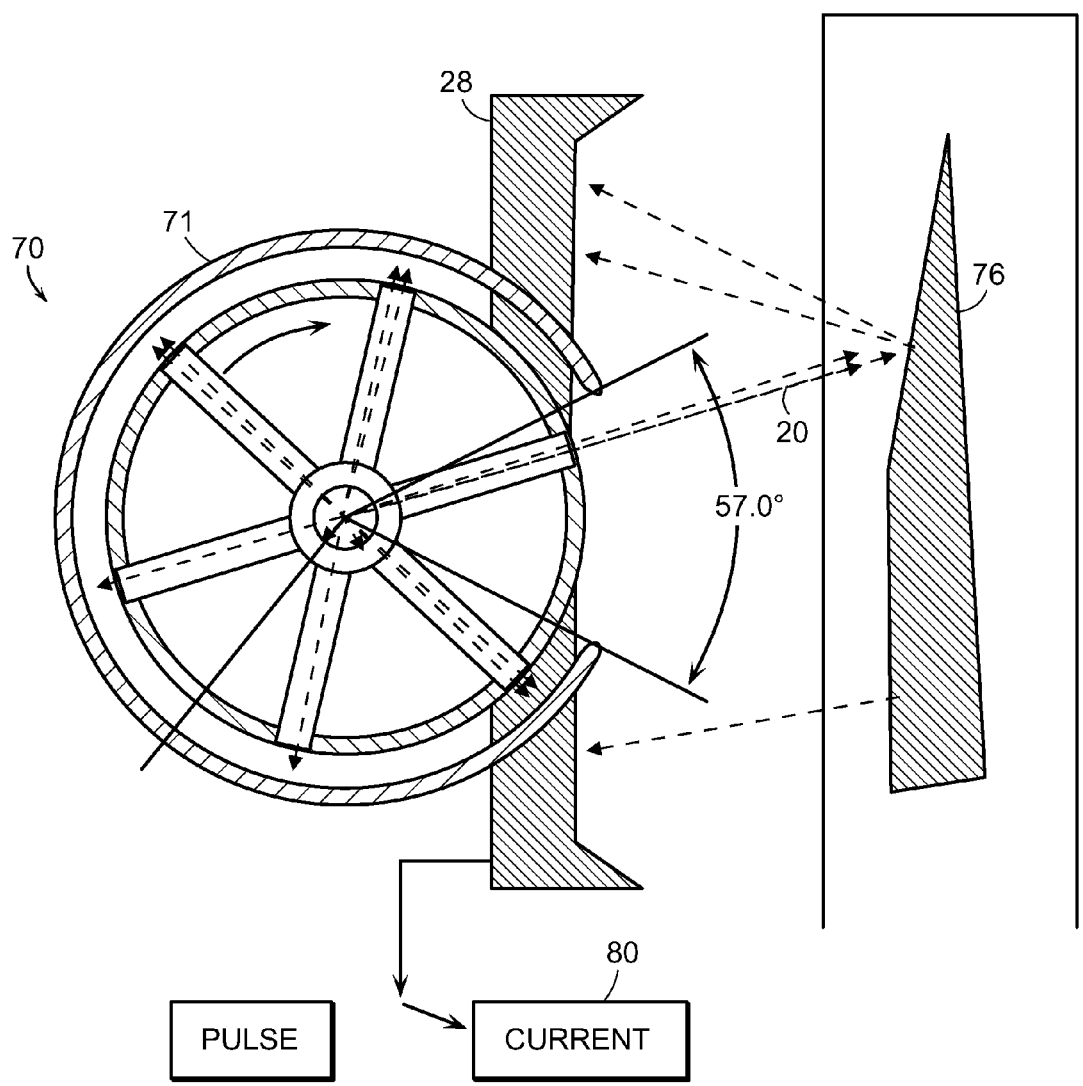
FIG. 3 depicts a passive method for detection of radioactivity in a mode in which the detector is sensitive mainly to Compton x-rays, according to an embodiment of the invention.

As shown in FIG. 3, the radiation detectors of certain x-ray inspection systems, measure current; i.e. the charge integrated over specific times, as measured by a current-integrating circuit 80. A current mode counter 80 sensitive to the fission material gamma rays may be implemented by the following method using a segmented detector having selective energy sensitivity.

Figure 4:
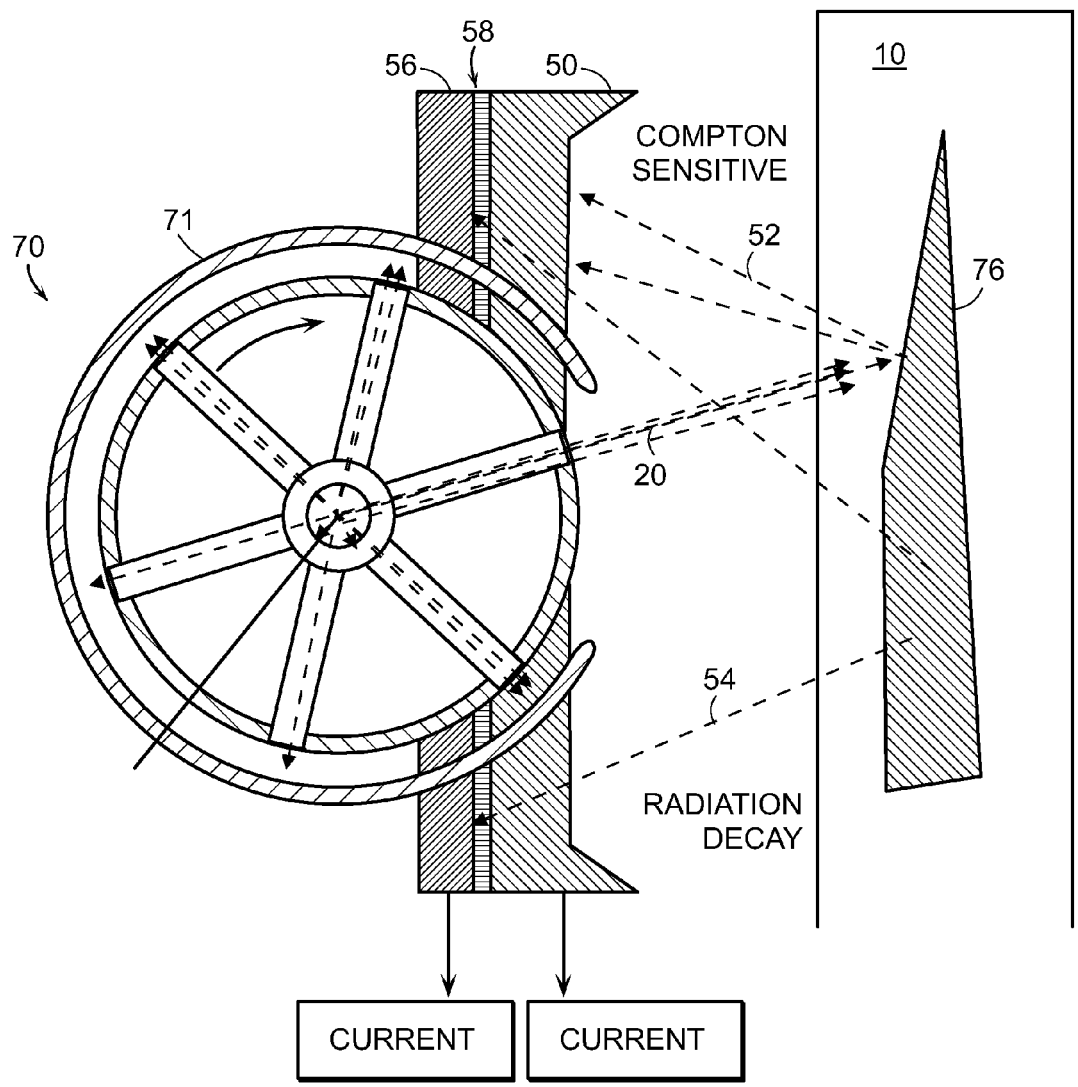
FIG. 4 depicts an active method of radiation detection using a two chamber detector to measure the emissions from fissile material, in accord with an embodiment of the invention.

Referring now to FIG. 4, a two-chamber backscatter detector is used. A front chamber 50, through which the fluorescing and fissile material radiation 52 and 54 pass through first, has very good efficiency for detecting the radiations below about 100 keV; i.e., the bulk of the Compton scattered radiation. A rear chamber 56, with thicker, higher-Z scintillators, has very good efficiency for detecting radiation up to 200 keV. An opaque wall 58 between the front and rear chambers may be an absorber properly chosen to further reduce the lower energy radiations while passing the higher energies that signify the presence of gamma rays emitted from container 10.

Figure 5:
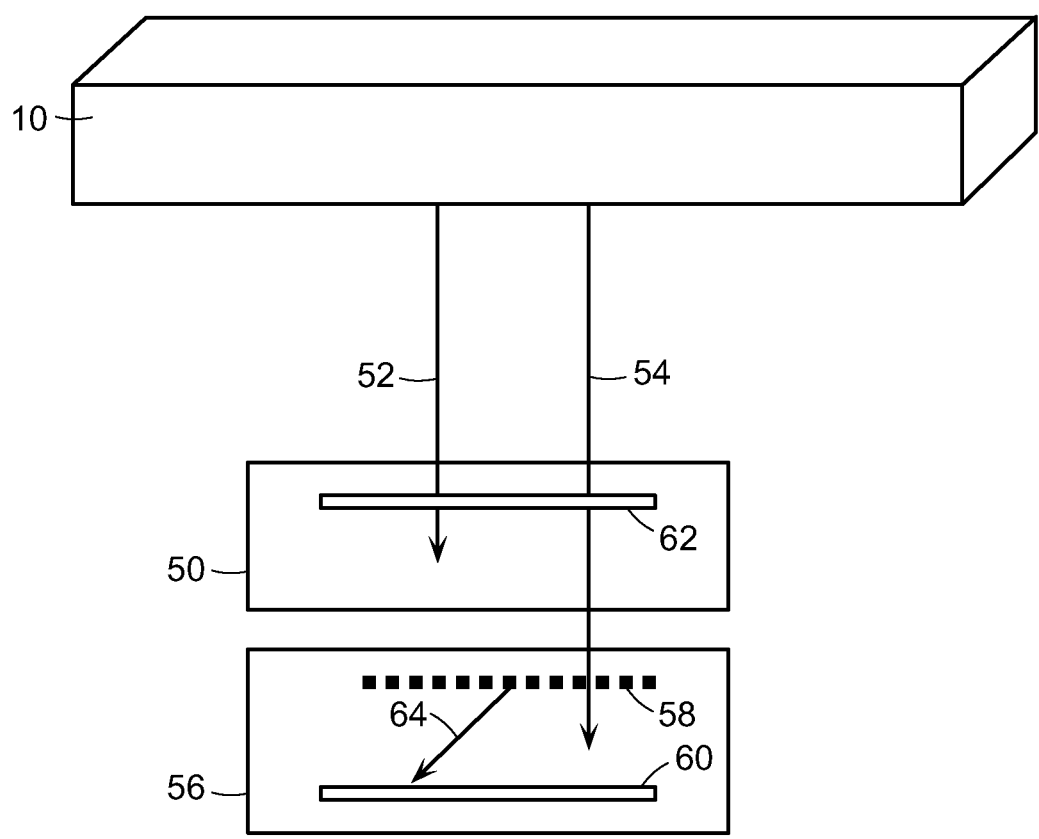
FIG. 5 is a schematic view of an embodiment of the invention showing a two-scintillation chamber detector configuration for detection of fissile material in accordance with an embodiment of the present invention.

The ratio of the current pulse in back detector 60 to that in front detector 62, as depicted in FIG. 5, is a good measure of the presence or absence of higher energy gamma rays. When there is no radioactive source in the inspected container, the ratio will have a range of values that will always be lower than the range of values when the gamma rays from uranium and plutonium are present.

In using the passive modes of detection, an alarm may be triggered by the system upon suspected detection of clandestine nuclear material. To verify the reality of an alarm, as determined by a high ratio, the x-ray beam may be switched off while the container is still in the inspection volume. This passive detection modality allows for a more careful measurement of the passive radiation emissions.
Active Detection:

Photoelectric interaction takes place in uranium and plutonium when the elements are bombarded with x-rays greater than 115.6 keV and 121.72 keV, respectively. The excited atoms then decay back to their ground states by isotropically emitting their characteristic $K_\alpha$ and $K_\beta$ x-rays. The energies of the $K_\alpha$ x-rays of U are 94.6 keV and 98.4 keV, while those of Pu are 99.4 keV and 103.7 keV. The energies of the $K_\beta$ x-rays of U are 111.3 keV and 114.5 keV, while those of Pu are 117.1 keV and 114.6 keV. These are characteristic x-rays with a uniquely high energy; the characteristic K x-rays of lead, the heaviest element that might be found in any quantity in a container, span the much lower range from 72.8 keV to 87 keV.

The x-ray generators used for inspecting luggage and smaller containers have maximum energies of 140 keV to 160 keV. The components of the x-ray spectrum above 115.6 keV and 121.72 keV (the K-electron binding energies of uranium and plutonium respectively) interact with the fissile elements through the photoelectric effect. The result is that the entire energy spectrum above the binding energies is effectively converted into the characteristic x-rays of the elements.

High-energy x-rays are readily detected with detectors operating in the pulse-counting mode, as known in the art. When the detectors are operated in a current integrating mode, it is necessary to use unorthodox methods.

The use of the simple two-chamber method described above in the context of passive measurements is typically not preferred here because the characteristic x-ray emission of the fissile material is at considerably lower energy than the gamma rays emitted by the fissile materials.

In accordance with a preferred embodiment, the two-scintillation chamber method described above is modified in the manner now discussed. Referring further to FIG. 4, front chamber 50 is, as before, especially sensitive to energies below 100 keV, while back chamber 56 is specifically sensitive to energies up to 130 keV. Cooled germanium detectors are preferably utilized, though other types of detectors may also be employed with such embodiments of the invention. The unusual feature of the back scintillation chamber, described now in reference to FIG. 5, is the inclusion of a layer of bismuth 58, approximately a mean free path thick, for energies above its K edge. X-rays below the K binding energy see the bismuth as a relatively thin absorber and the photoelectrically induced L x-rays have too low an energy to be effectively detected. Alternatively, other heavy metal materials such as lead or gold may be used in place of bismuth. X-rays above 90.5 keV, however, are converted into x-rays of 74.8 keV and 89.8 keV, which are detected in scintillation detectors of the back detector. The conversion efficiency depends on the energy of the x-ray or gamma ray being converted; it is ~50% for 185.6 keV. When no fissile signal is present, the ratio of the current integrated signals in the back detector to that of the front detector is lower than the ratio when fissile material is present. Thus the ratio can be used to automatically alarm on the presence of fissile material. Sensitivity to 100 gram amounts of fissile material is readily achieved.

A simple calculation, referring to FIG. 5, shows the effectiveness of a two-chamber method of detection. Ray 52 represents backscattered radiation from a container 10 that has negligible fissionable material or any very heavy element such as lead or gold. The spectrum of backscatter 52, generated from an x-ray generator with a maximum electron energy of 160 keV, has few x-rays above 100 keV. Typically, for every 100 x-ray photons with energy in the range of 60 keV to 75 keV, there will be less than 5 x-ray photons above 100 keV. Ray 54 represents backscatter and additionally K x-rays fluoresced from fissile material in container 10.

Front chamber 50 has a scintillator 62 of, for example, 200 mg/cm$^2$ of GdOS, which has an efficiency of ~70% for counting the 60 keV to 75 keV radiation, but only a 30% efficiency for counting the x-rays above 100 keV. Thus, the signal in chamber 50 will consist of 70 counts from the 60 keV to 75 keV x-rays and 1.5 counts from the x-rays above 100 keV. Passing out of chamber 50 into chamber 56 are 30 x-rays in the 60-75 keV range and 3.5 x-rays above 100 keV.

The x-rays that enter chamber 56 pass through a bismuth absorber 58 which has a 70% efficiency for stopping the x-rays in the 100 keV to 120 keV range and a 50% efficiency for stopping the x-rays in the 60 keV to 75 keV range. Thus 15 of the 30 x-rays of 60-75 keV stop in the bismuth; the produced L x-rays have too low an energy to be counted in the scintillator 60. Scintillator 60 is similar to scintillator 62 and it therefore counts ~10 x-rays of 60-75 keV and less than 1 x-ray greater than 100 keV. The ratio of counts in chamber 56 to chamber 50 will be 10/70=~0.14; the ratio of currents will be almost the same.

The case when fissile material is present is now considered, with shielding around the fissile material neglected for clarity. A 140 keV x-ray beam produces approximately 500 characteristic fluorescence x-rays 54 from every square centimeter of uranium or plutonium that is struck by the beam. Approximately 100 of those fluorescence x-rays will enter chamber 50 and 30 of them will stop and be counted. The total counts in chamber 50 will then be 70+1.5+30=101.5.

The 70 fissile-induced x-rays 52 that penetrate into chamber 56 will interact with the bismuth and 50 of them will stop and produce bismuth x-rays 64 of 75 keV to 100 keV. These will be counted in chamber 56 with an efficiency of ~70% so that the bottom chamber will count ~35 x-rays over and above the count were fissile material to be absent. The ratio of counts, or current, between chamber 56 and 50 will rise from ~0.14 to almost 0.5, a readily distinguished change. Use of a pencil beam for x-ray irradiation of the inspected enclosure allows determination of the outline and position of the fissile material, using standard x-ray inspection algorithms. Upon detection of fissile material, processor 42 (shown in FIG. 1) may then give rise to activation of an alarm 43, and, additionally, display the outlines of the fissile material on display 44 using highlighting coloring or other standard techniques.

It is also to be noted that some of the active modes described herein may equally be used to detect high atomic number shielding materials, such as lead or tungsten, enabling the detection of clandestine shielded radioactive sources. For example, lead shielding, which may be used to conceal radioactive sources, may be detected using these methods since the lead atoms emit signature fluorescence x-rays at 72.8 keV to 84 keV when excited by x-rays with an end-point energy of 225 keV. Similarly, tungsten emits fluorescence at 59.7 keV to 67 keV when excited by an x-ray beam with end point energy of 225 keV. Thus, heavy metal shielding may be identified based on identifying the specific energy of active x-ray fluorescence expected from an interaction between the heavy metal shielding and the exciting x-rays. Alternatively, the excitation of the heavy metal shielding may result is a distribution of fluorescence photon energies, which may be used to identify the presence of the shielding.

It is to be noted, also, that the passive and active modes described herein may advantageously also be employed in conjunction with x-ray inspection systems employing a fan beam, or otherwise shaped beams, such as standard transmission-imaging systems commonly employed for luggage scrutiny at airports. The preferred position, however, for the fission detectors is in the back direction, i.e., on the same side, with respect to the inspected object, as the x-ray generator. In that geometry, the energy of the x-rays Compton-scattered from material in the container will be lowest and furthest in energy from the high-energy characteristic x-rays, or gamma rays, emanating from the fissionable material.

In other embodiments of the invention, the passive and active modes described herein may be enhanced through the use of conventional x-ray imaging capabilities of an inspection system. For example, the active and passive modes may include the use of an alarm (e.g., an optical or audio signal) to indicate that a detection signal is triggered at least in part by the presence of clandestine nuclear material. Upon the triggering of an alarm, the x-ray image corresponding to the scanned object may be examined to determine the location, shape, or other characteristics of the clandestine nuclear material. As well, the x-ray image may be used to reposition the scanned object or container to increase the efficiency and accuracy of detecting clandestine nuclear material. In the passive modes, this may include positioning detectors to detect emissions from to suspected clandestine material. In the active modes, this may include positioning a scanning x-ray beam to excite the suspected clandestine nuclear material and positioning a detector to detect the fluorescence.

Designs for Neutron and Radiation Detectors

Embodiments of the invention discussed herein may be utilized to improve the detection of clandestine nuclear sources. In particular, some embodiments may be utilized in conjunction with the modes described earlier to detect clandestine nuclear material.

Some embodiments of the current invention are directed toward the detection of thermal neutrons. Thermal neutrons fluxes above the low ambient background are produced by specific radioactive sources, so-called AmBe and PuBe sources, or by the spontaneously fissioning isotope $^{244}$Cf, or by sources of plutonium; the detection of the latter being prima facia evidence for atomic bomb material. Commercial sources of thermal neutrons are rarely found outside fixed installations so that the presence of thermal neutrons above the ambient levels is cause for alarm. Thermal neutrons have traditionally been detected by commercially available $^3$He or $BF_3$ counters or by plastic or glass scintillators doped with $^6$Li or $^{10}$B.

In embodiments of this invention, the neutrons are detected in special large area scintillator screens that have a higher efficiency for detecting thermal neutrons than detecting x-rays or gamma rays. Such embodiments may be used in connection with a conventional x-ray imaging system (e.g., a system as depicted in FIG. 1 and described earlier) to search for clandestine nuclear material that includes a neutron emitter. A preferred embodiment makes use of material that is more sensitive to thermal neutrons than backscattered x-rays, with a detection ratio greater than approximately $10^6$. An example of such material is a 20 mg/cm² gadox scintillation screen. Gadox ($Gd_2O_2S$) has a high efficiency for detecting thermal neutrons, but a low detection efficiency for detecting x-rays; it is almost transparent to photons above about 100 keV. The different mean free paths between thermal neutrons and particular energies of x-rays can be used to make a "$4\pi$" neutron only detector, or a directional neutron detector, or a "$4\pi$" neutron plus x-ray detector, or a directional detector for both x-rays and neutrons, as discussed in greater detail below. Though some embodiments of the invention described herein refer to the specific use of gadox as a neutron and radiation scintillator, it is readily understood by those skilled in the art that the embodiments are not limited to the use of gadox, and may be practiced with any material with appropriate neutron or radiation interaction properties adjusting for the appropriate mean free path of neutrons and photons. Of particular interest are the $^6$Li-based scintillation screens (e.g., LiF) which have good efficiency for detecting thermal neutrons, i.e. 30% or greater, while being virtually invisible to x-ray or gamma ray radiation. Another neutron detector of interest is a high pressure $^3$He proportional counter.

The detection of gamma radiation may be accomplished using detectors that are also used to create the backscatter and transmission x-ray images. The backscatter detectors, which typically consist of a barium based scintillator (e.g., $BaFCl_2$ phosphor screen), are most efficient for detecting the lower energy gamma rays, in the energy range below about 100 keV. The transmission detector, which consists of plastic scintillator, is most efficient for detecting the higher energy gamma rays above about 150 keV.

In some embodiments of the invention, a high-energy detector may be added behind or beside the x-ray backscatter detectors used to form a backscatter image of the x-rays 20. This addition is especially important when embodiments of the invention do not utilize a transmission imaging detector. The high-energy system may be one of many types of commercially available gamma detectors, including NaI (Tl), BGO, CsI(Tl). In a preferred embodiment, the gamma ray detector is a segmented, large area plastic scintillator that is very well shielded from gamma radiations of energies below 200 keV; a segmented large area liquid scintillator may also be appropriate in some applications.

The plastic or liquid scintillator approach is attractive for several reasons. The cost per unit area for plastic or liquid scintillators is by far the lowest for detectors of the same efficiency. Plastic or liquid scintillators have very poor energy resolution and will not be able to identify the radioactive element that emits the high-energy photons it detectors. But they will serve the purpose of quickly and efficiently finding, hidden high-energy gamma ray sources such as $^{137}$Cs or $^{60}$Co. Identifying the isotope will be the task of an auxiliary detector that may be a hand-held probe with good resolution that can identify the emitting isotope. The segmentation of the plastic or liquid scintillator is preferably along the direction of travel of the container so that, knowing the speed of the container moving by the detector it is straightforward to determine the approximate origin of the radioactive source in the container.

The plastic or liquid scintillator has the further important advantage that it can serve the dual purpose of an efficient gamma ray detector and an efficient moderator of fast neutrons. A preferred embodiment uses a segmented plastic or liquid scintillator with a total area that is equal to, or greater than, the area of the neutron detector and placed just in front of the neutron detector, that is, on the side facing the target volume.

In some embodiments of the invention, a neutron detector may be operated simultaneously with an x-ray imaging inspection system. The following description uses the scintillator gadox as the example of an efficient neutron detector. It should be understood that other neutron detectors, known in the art, could serve as well or better. For example, $^6$Li is incorporated in some scintillation screens to give good neutron detection efficiency. The large energy released when $^6$Li captures a neutron can be used to discriminate neutron from photon interactions, making the screens invisible to gamma radiation. The methods of making a $^6$Li detector sensitive to the neutron direction would be similar to those described below for gadox.

Figure 6:
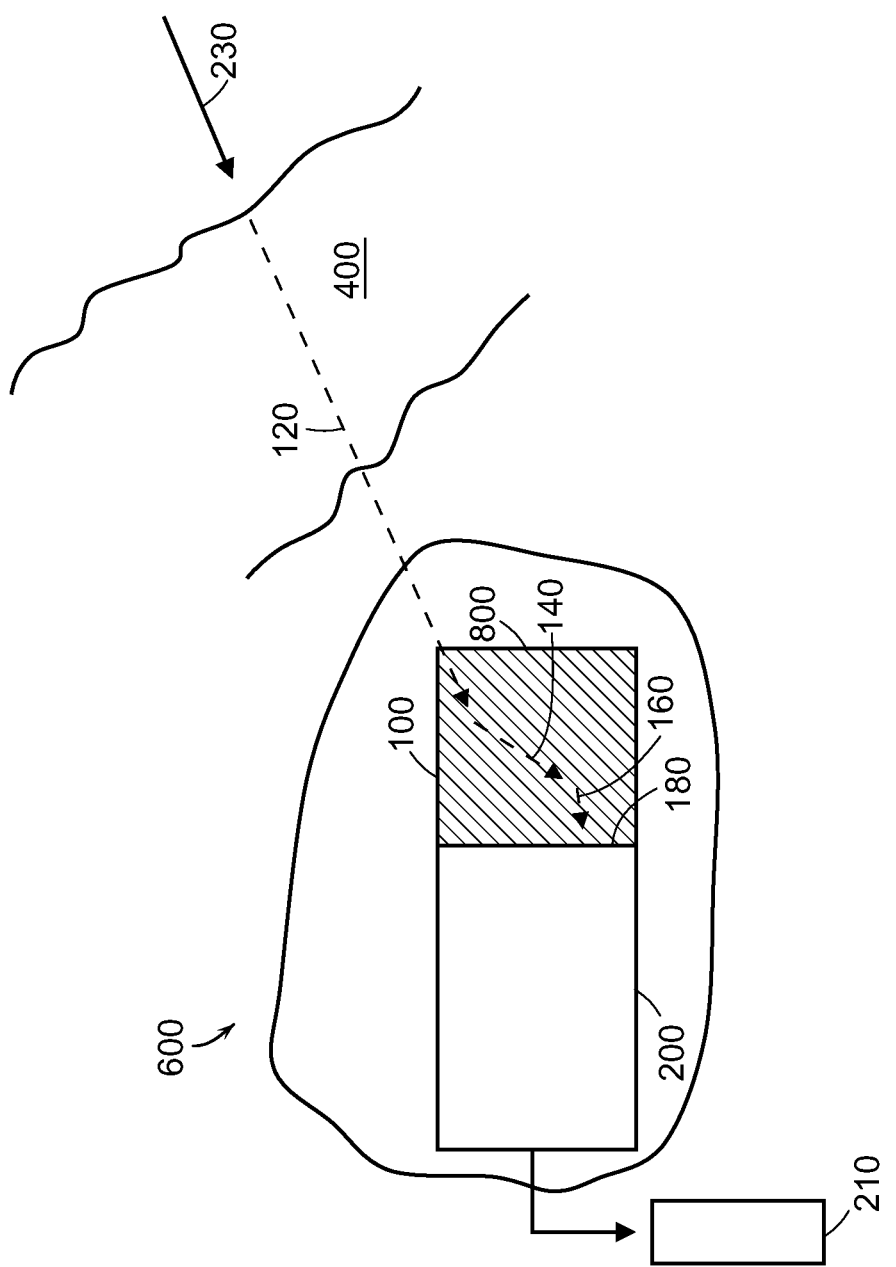
FIG. 6 is a schematic view of essential elements of a thermal neutron detector in accordance with preferred embodiments of the present invention.

FIG. 6 shows the essential elements of a neutron detector 600. A gadox scintillator screen 100, covered by an optical shield 800 that reflects the internally generated light, is viewed by a PMT 200. Thermal neutrons entering the gadox 100 along path 120 are absorbed by the $^{157}$Gd, producing Auger (internal conversion) electrons 140 with energies in the 24 to 70 keV range. These electrons 140 stop in the gadox 100 producing optical photons 160. The optical photons 160 are captured by the photocathode 180 of the PMT 200, producing a signal at the anode that is processed by pulse electronics 210. The neutrons 120 are stopped in the first 20 mg/cm² of the gadox 100. The optical photons 160 have a maximum travel of about 200 mg/cm² in gadox. A region 400 of a moderator material, such as paraffin, for example, may be provided in order to slow any fast neutrons 230 and enable their detection in the manner herein described with respect to thermal neutrons.

If the gadox is thicker than the maximum optical photon travel distance, then neutrons stopping in the outer layer are not detected. Neutrons entering the gadox from the side facing the PMT photocathode are readily detected.

Figure 7:
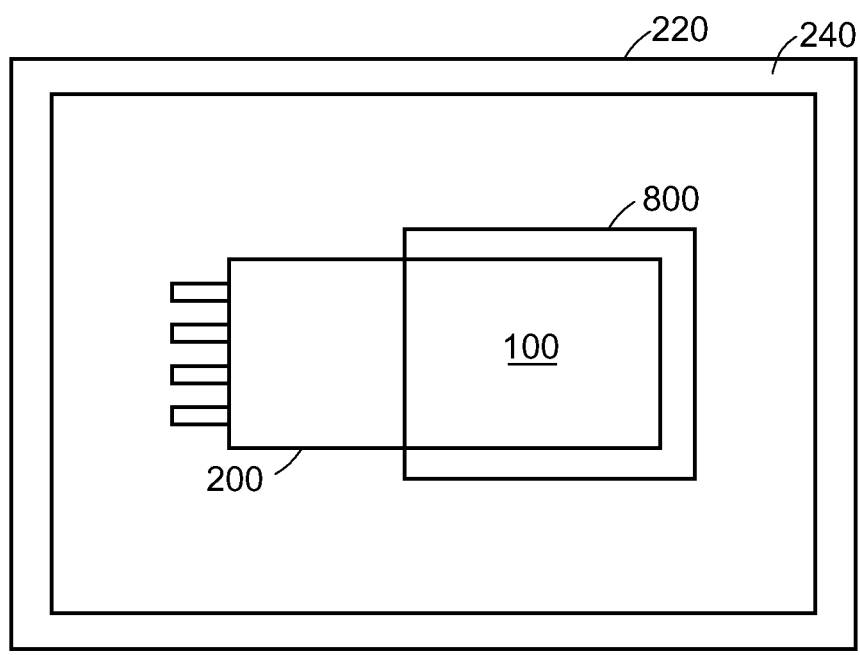
FIG. 7 is a schematic view of a 4π thermal neutron detector in accordance with embodiments of the present invention.

Referring now to FIG. 7, an embodiment of the invention in the form of a "4π" neutron-only detector is made by placing a 20 mg/cm$^2$ thick gadox screen 100, with its accompanying optical shield and reflector 800 and photodetector(s) 200, in a box 220 shielded by a material 240 opaque to x-rays. Shield 240 may be 5 mm thickness of bismuth or 1 cm of lead, to cite two examples. Bismuth, with a mean free path of 17 cm for thermal neutrons, is essentially transparent to the neutrons but effectively shields the gadox from x-rays and gamma rays that have any appreciable interaction with the gadox.

To make a directional detector of neutrons, the gadox need only be much thicker than the mean free path of the optical light, say 300 mg/cm$^2$. The light detected by a PMT must have come from neutrons that entered from the side of the gadox facing the photocathode of the PMT. This embodiment, when unshielded with respect to x-rays, is also a directional detector for x-rays that have a mean free path much less than 150 mg/cm$^2$ in gadox. And when this detector is placed in a properly shielded box, it may be rendered sensitive to neutrons only.

Other materials that may be used to shield neutrons include $^6$Li, $^{10}$B, $^{113}$Cd, and $^{157}$Gd.

In another embodiment of the invention, neutron detection may be enhanced by combining a neutron detector with an x-ray scanning system to aid identification of the location of a neutron source associated with a scanned object or container. An x-ray scanning system may translate an object relative to a neutron detector. Thus, the counts of a neutron detector and the position of a scanned object or container may be correlated to identify the location of a neutron emitter associated with an object or container. If imaging is part of the x-ray scanning system, the generated image may also be correlated with the counts of the neutron detector to improve the ability to locate the neutron emitter. Other more precise detectors may also be subsequently utilized to further characterize or confirm the detection of a neutron emitter.

Alternative versions of the invention for detection of neutrons and x-rays make use of back-to-back gadox screens separated by an opaque film, or combinations of gadox and scintillation screens that do not contain gadolinium and are essentially transparent to neutrons.

In accordance with further versions of the invention, a moderator, such as paraffin, is employed to convert fast neutrons into thermal neutrons. Thus, fast neutrons, such as those emitted by plutonium, may advantageously be detected in the manner described above with respect to thermal neutrons. Examples of other moderator materials include materials containing hydrogen, including high density polyethylene and water.

Another embodiment of the invention utilizes a moderator that may also act as a high energy photon detection screen. Plastic or liquid scintillators may be used to capture high energy photons (e.g. photons with energies above 200 keV), while also slowing fast neutrons. The thickness may be tailored to the particular application; for some of the examples discussed herein, plastic or liquid scintillators with thicknesses in the range of approximately 2 cm. to 10 cm strike the correct balance of moderating neutrons and allowing lower energy photons to pass through. Such a moderator may also be segmented. The moderator is typically arranged serially with a neutron scintillator to moderate neutron velocity before the neutrons impinge upon the neutron scintillator.

Figure 8:
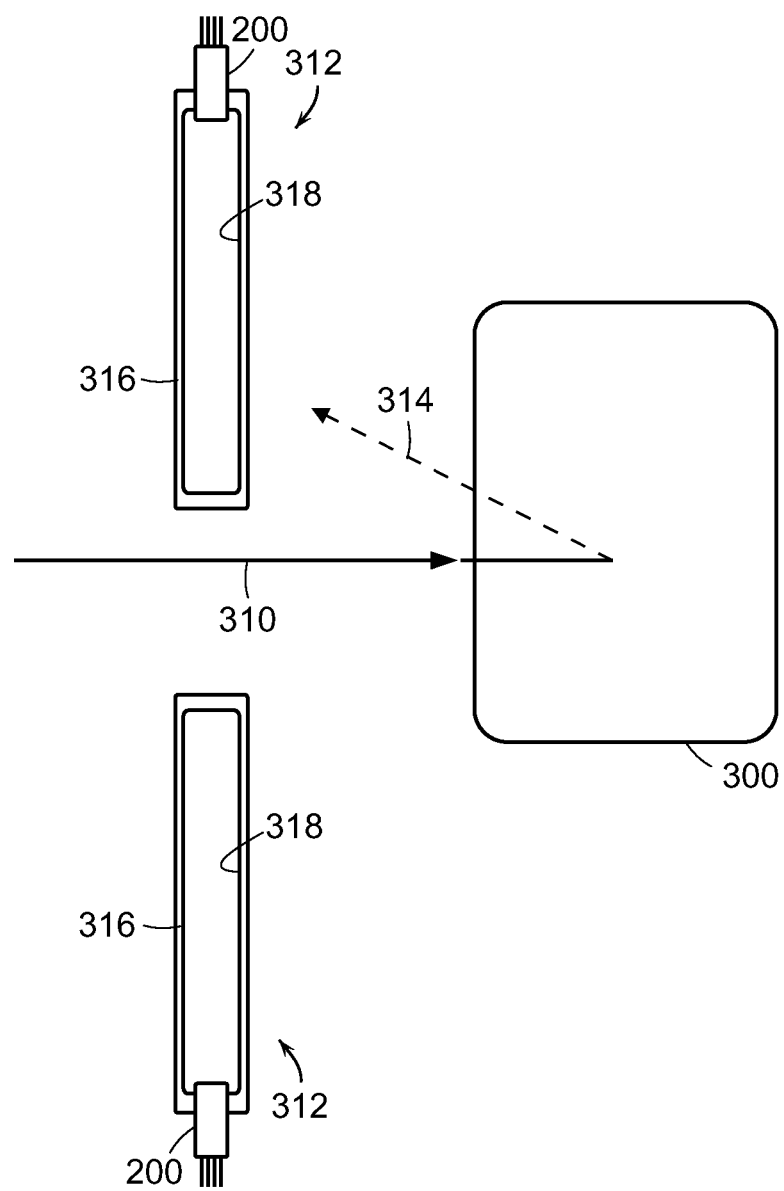
FIG. 8 is a schematic view showing the use of backscatter detectors of a cargo inspection system for detection of thermal neutrons in accordance with preferred embodiments of the present invention.

One preferred embodiment of the gadox detectors is in x-ray inspection systems to find neutron-emitting material in baggage at airports or in freight cargo. Referring now to FIG. 8, baggage or cargo 300 is irradiated by x-ray beam 310, typically swept as a pencil beam in a scanning pattern across object 300. Other beam shapes, however, are within the scope of the present invention. Detectors 312 of backscattered x-rays 314 are hollow rectangular boxes whose inner surfaces are lined with gadox 316, approximately 150 mg/cm$^2$ thick, or, alternatively, gadox and another scintillator that does not absorb neutrons. Photomultipliers 200 intrude into the boxes to detect the fluorescent light. In order to transform the backscatter detectors into efficient neutron detectors as well as x-ray detectors, the gadox 318 on the surfaces facing the inspected container 300 are thin enough that fluorescent light from the neutrons stopped in the outer 10 mg/cm$^2$ layer can efficiently escape out of the scintillator and be detected by the PMTs. A more effective solution is to add a separate section to the backscatter detectors with additional PMTs.

Alternatively, thick gadox can be placed on the surface furthest away from the inspected container, and a scintillator that is essentially transparent to neutrons can be placed on the surface facing the inspected container. In this embodiment, the neutrons will be absorbed on the inner surface of the gadox, allowing the scintillation light to be detected by the PMTs. Gamma rays and x-rays will be absorbed and detected in both the gadox and the other scintillator. In this way, the efficiency for absorbing and detecting high energy x-rays or gamma rays may be maximized.

Gadox scintillation screens can be placed, in accordance with other embodiments of the invention, on traditional gamma ray detectors that have excellent efficiency for detection of both high and low energy x-rays or gamma rays. In this embodiment, the gamma ray detectors act as light conduits for the fluorescent light produced by the gadox screens. For example, the gadox can be optically coupled to plastic scintillators viewed by PMTs to efficiently detect high energy gamma rays. Alternatively, the gadox can be optically coupled to high-Z gamma ray detectors such as NaI(Tl), BGO, CsI(Tl), etc. The signals from the two distinct scintillators, one of which is gadox, can generally be viewed by a single PMT with the signals from the two scintillators distinguished by their different pulse decay times, a technique well known in the art. When two distinct scintillators, one of which is gadox, are viewed by two PMTs, the signals from the two scintillators can be separated by placing a notch filter for the 511 nanometer line on one of the PMTs so that it only counts light from the gadox.

Gamma Ray Detection Enhancement

In accordance with further embodiments of the invention, the detection efficiency of scintillation screen detectors is enhanced for x-rays above about 70 keV, with particular utility for x-ray energies in the 100 keV to 200 keV range.

Advantage is taken of the fact that heavy materials such as tungsten, lead and uranium are excellent converters of higher energy photons to lower energy photons, which, in turn, are more efficiently detected by the gadox. The invention is now described with reference to the schematic shown in FIG. 9.

X-rays 420, 440, 480 or gamma rays 420, 440, 480 impinge on the detector 410, which consists of a scintillator 370, such as gadox, lining the inside of the front face, a scintillator 320, such as gadox, lining the inside of the back face of the detector, PMTs 360 viewing the interior of the detector to measure the intensity of the light emitted from the gadox, and a sheet 340 of a heavy element, such as lead, backing the scintillator 320.

The operation of the detector is illustrated by imagining that 100, 100 keV x-rays (such as the K x-ray of uranium) and 100, 185.6 keV gamma rays (from the decay of fissionable $^{235}$U) impinge on the detector. The screens 370, 320 are assumed to be 150 mg/cm$^2$ gadox, their maximum effective thickness. The backing 340 is assumed to be 5 mm of lead, which is thick enough to stop the 100 keV and 185.6 keV photons. We consider each radiation in turn; the numbers in the examples are approximations provided solely for purposes of illustrating the principles described herein.

The front gadox layer 370 stops and detects about 30 of the 100 keV x-rays, letting 70 x-rays through. The back gadox layer 320 stops 21 of the 70 x-rays so that if the lead sheet 340 were not present, 49 x-rays would pass out the back end of the detector; the efficiency of the detector for 100 keV x-rays would be ~50%.

Figure 9:
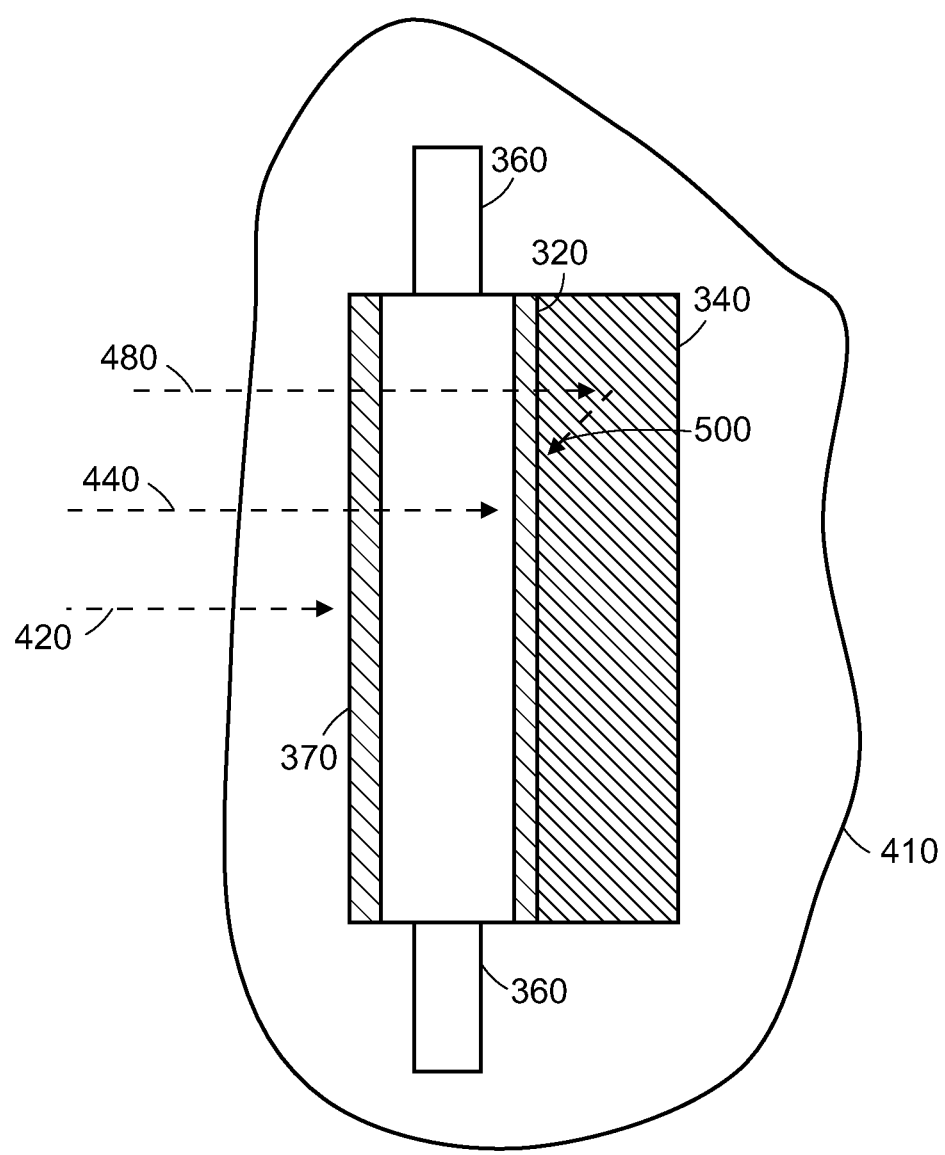
FIG. 9 is a schematic view of essential elements of an enhanced x-ray or gamma ray detector in accordance with preferred embodiments of the present invention.

In the configuration of FIG. 9, the remaining 100 keV x-rays 480 stop in the lead sheet, 340. The stopping is primarily the result of the 100 keV x-rays ejecting K electrons 500 from the lead atoms (the photoelectric effect). When the excited lead atoms deexcite, which they do in less than a picosecond, K x-rays are emitted with energies of 72 and 75 keV; for illustration we use the dominant 75 keV x-ray. The fraction of incident x-rays that result in K x-rays emitted backwards into the detector is given by the ratio, $$F \sim \mu(\text{photoelectric})/[\mu(\text{total for 100 keV})+\mu(\text{total for 75 keV})]=0.68.$$

The actual fraction will be lower because of the finite angular spreads and the finite fluorescent yield, but will still be close to 50%. Thus, about 25 of the 49 x-rays that entered the lead backing will result in 72-75 keV x-rays reentering the chamber. The 300 mg/cm$^2$ of gadox captures 80% of these x-rays so that ~20 of the 49 x-rays are detected. The lead backing has increased the efficiency of the detector for 100 keV x-rays from 50% to 70% at a cost of a sheet of lead.

The calculation for the 185.6 keV gamma ray impinging on the detector proceeds similarly. Of the 100 incident gammas, only 9% interact at all in the gadox, so that more than 90 gamma rays penetrate into the lead. Approximately 30% of these gamma rays produce lead K x-rays that reenter the backscatter detector. The result is that approximately 20 additional gamma rays are detected over what would have been detected without the lead. The efficiency of the detector has increased from 9% to 29% by the addition of a sheet of lead.

Combined Neutron Detector and Enhanced Gamma Ray Detector

Figure 10:
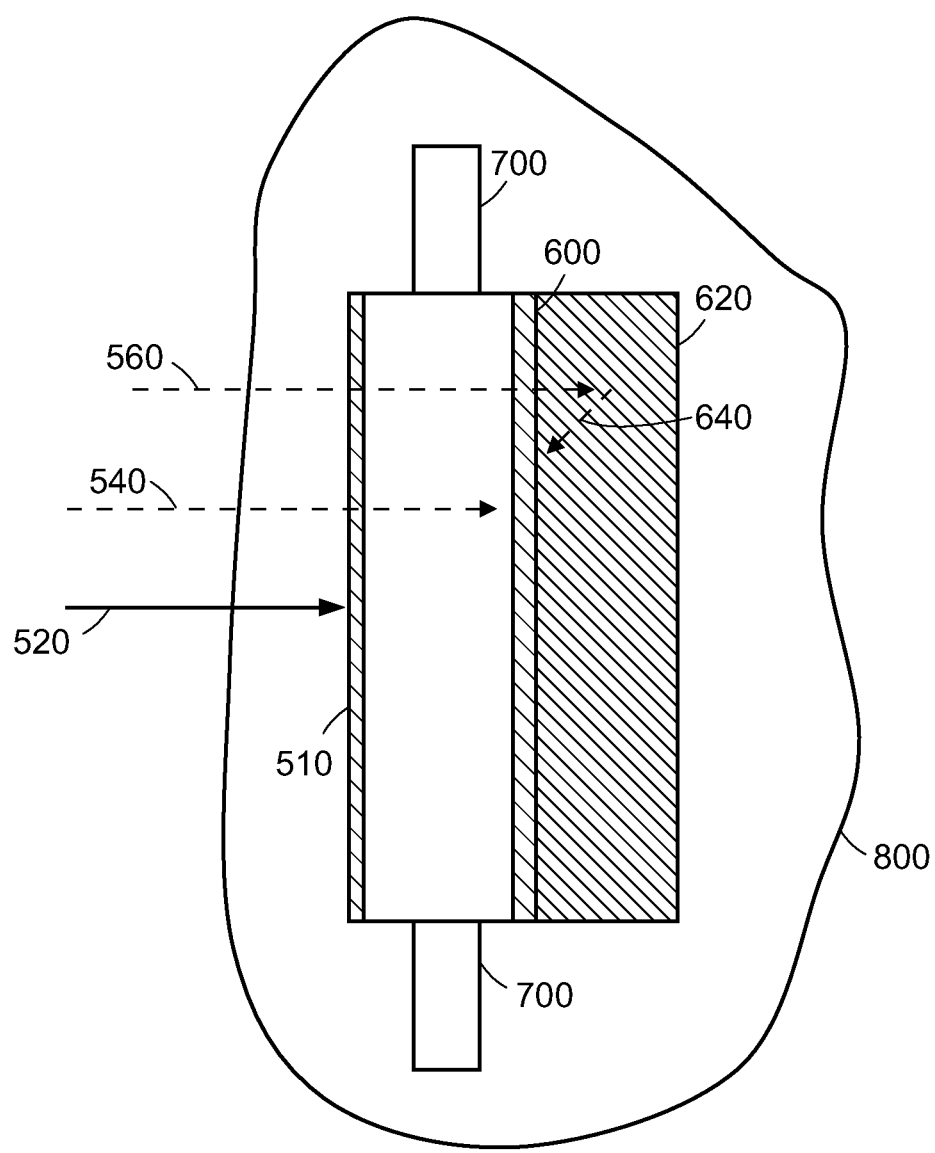
FIG. 10 is a schematic view of a combined enhanced photon detector and thermal neutron detector in accordance with further embodiments of the present invention.

The invention described herein is advantageously applied to the efficient detection of fissionable material that may be transported illegally by smugglers or terrorists. FIG. 10 shows a simple detector 800 that has excellent efficiency for thermal neutron capture, and good efficiency for both the K x-rays of uranium or plutonium and the 185.6 keV gamma rays emitted by fissionable uranium. Detection of fast neutrons by employing an intervening moderator is discussed elsewhere herein.

The configuration is similar to that of FIG. 9, the only substantive difference is that the first gadox layer 510 is only 20 mg/cm$^2$ thick. The front layer stops the thermal neutrons 520 producing strong signals in the PMTs 700 corresponding to the deposition of 25 keV and 70 keV electrons. A fraction of the 100 keV and 185.6 keV photons 540 stop in a back scintillator layer 600, the remainder stop in the lead backing 620. The back scintillator layer 600, in accordance with one embodiment, may itself be gadox or another high-neutron-capture material, and, more specifically, may have a thickness of 150 mg/cm$^2$.

The overall detection efficiency for the 100 keV and 185.6 keV radiations is about 60% and 25% respectively. The detection efficiency for thermal neutrons is ~50%.

Other configurations of successive scintillator panels are also within the scope of the present invention. If the first detector is thin gadox then the second detector can be any scintillator with good stopping power, including gadox. Alternatively, the first detector may be a scintillator other than gadox while the second detector is gadox.

If the second detector is gadox, then, within the scope of the present invention, the first detector can be thin gadox or a scintillator other than gadox.

In another embodiment of the invention, the front layer 510 is a neutron scintillating material with a low efficiency for capturing gamma-rays or x-rays below a given threshold energy. The second layer 600 is a scintillator with a higher efficiency for capturing gamma-rays or x-rays above the given threshold, while having poor to zero efficiency for capturing neutrons. The capture of photons 560 by the second layer 600 may be enhanced by employing a heavy metal backing 620 that is chosen to produce Auger electrons 640 that are subsequently absorbed by the second layer 600, in a manner similar to what is described earlier.

Figure 11:
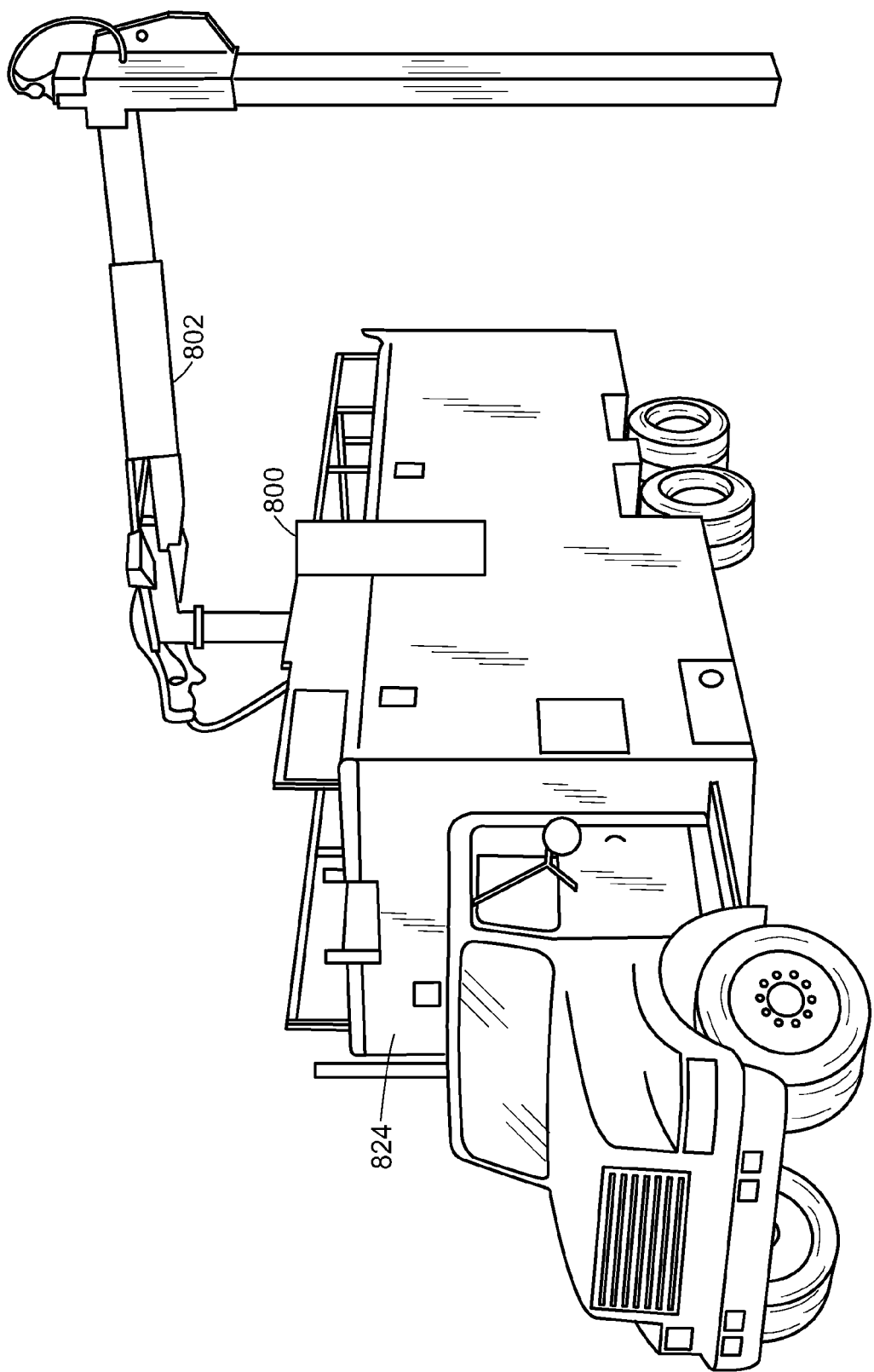
FIG. 11 is a perspective view of a mobile cargo inspection system deployed on a truck capable of on-road travel to a location where the same truck may be used to scan an enclosure such as a vehicle or cargo container in accordance with preferred embodiments of the present invention.

Some embodiments of the invention make use of systems in which detectors are deployed at a fixed site, as may be appropriate for the screening of parcels or baggage, such as mail shipments or luggage carried by passengers. Other preferred embodiments of this invention make use of systems in which detectors are mounted on a mobile platform, typically capable of road travel, that traverses a large object to be inspected such as a vehicle or a cargo container. FIG. 11 shows such a system of the mobile sort, by way of example, wherein detectors contained within detector modules 800 and 802, as further described below, are carried by, or otherwise coupled to, truck 824 which traverses an enclosure to be inspected during the course of the inspection. The detectors may be sensitive both to emission naturally emitted by threat materials as well as to penetrating radiation that is emitted by a source carried by, or otherwise coupled to, truck 824, after the penetrating radiation has interacted with the object under inspection.

Inspection systems that may be used for practice of the present invention are of particular utility for the inspection of large cargo containers such as trucks or sea/air containers in that they employ mobile platforms that may be driven past the inspected container during the course of the inspection. Such systems are described in U.S. Pat. No. 5,764,683 (Swift et al.), issued Jun. 9, 1998, which is incorporated herein by reference.

Figure 12:
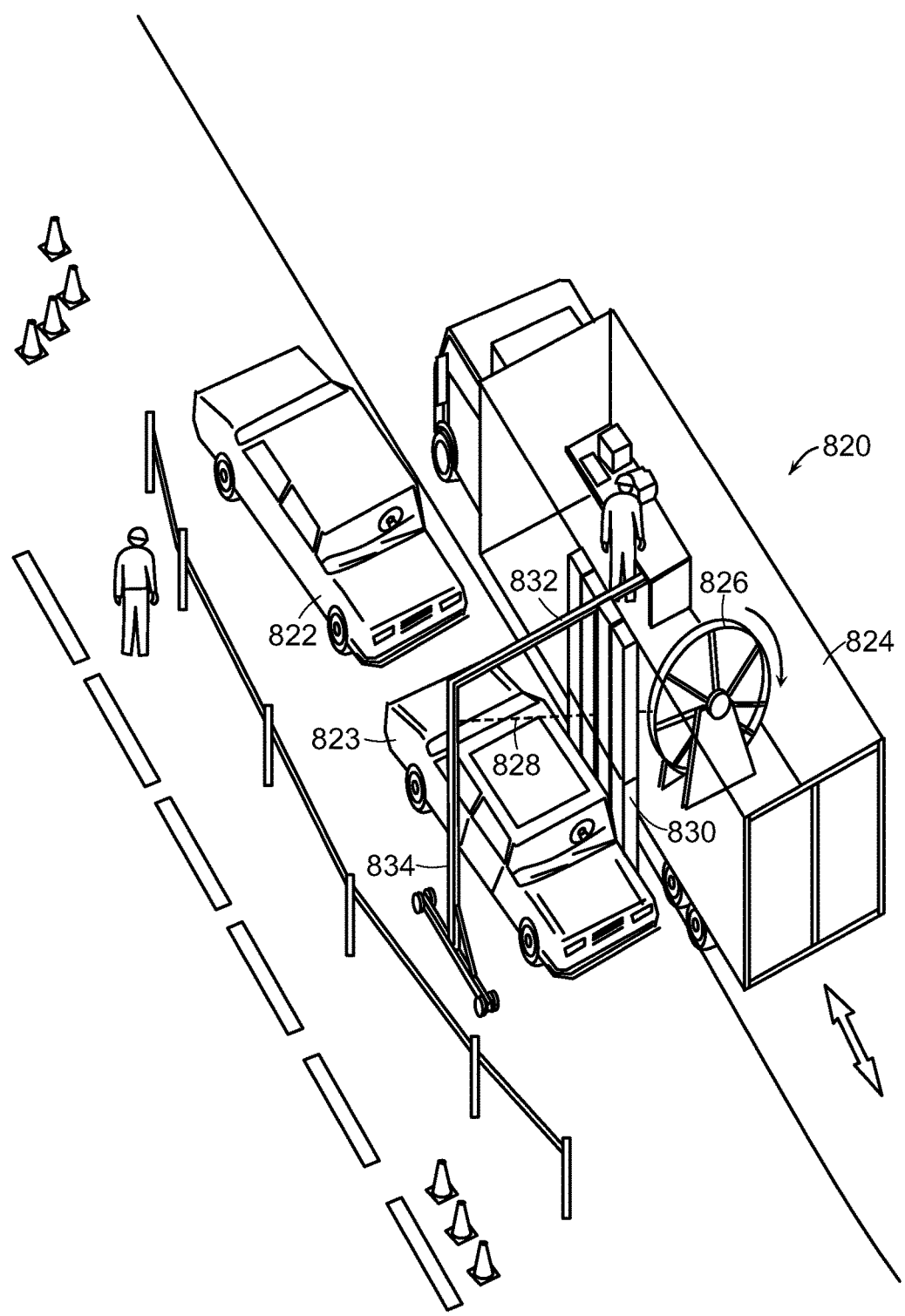
FIG. 12 is a perspective view of the device of FIG. 11 for inspecting vehicles or large containers for nuclear threats in accordance with embodiment of the invention.
Figure 13:
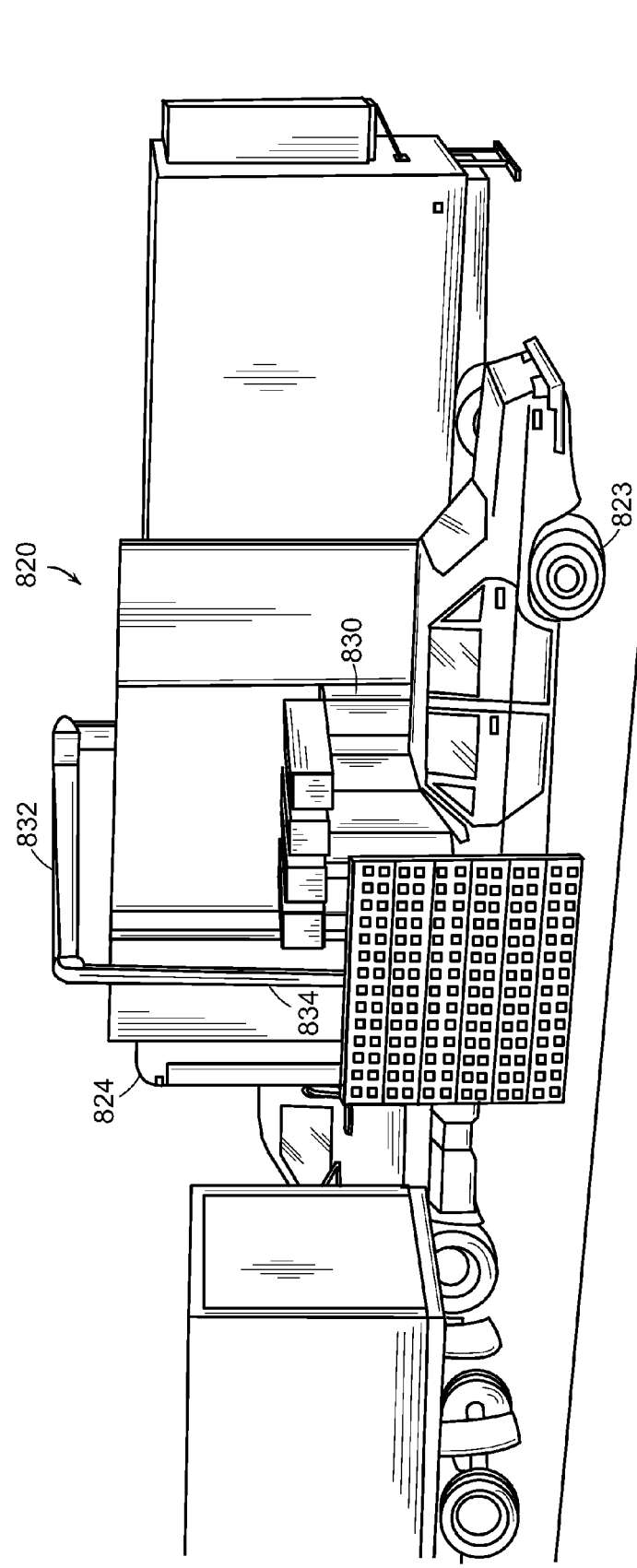
FIG. 13 is a side view of a further embodiment of a device for inspecting a large container in accordance with the invention.

In FIG. 12, cargo container inspection system 820 is shown deployed for inspection of passenger cars 822 and 823. FIG. 13 shows another embodiment of the invention that may advantageously be employed for the inspection of passenger vehicles.

With reference to FIGS. 12 and 13, a truck 824, typically 35' long×8' wide×10'6" high, houses and supports the x-ray inspection equipment, ancillary support and analysis systems, and a hydraulic slow-speed drive mechanism to provide the scan motion. Truck 824 serves as both the platform on which the mobile system is transported to its intended operating site, and a bi-directional translation stage, otherwise referred to herein as a "bed," to produce the relative motion required during a scan. Chopper 826 (shown in FIG. 12) is used, in accordance with flying spot generation (discussed above in reference to FIG. 1) to scan beam 828 of penetrating radiation recursively in a vertical direction. Radiation scattered by the contents of the cargo container, shown here as passenger car 823, is detected by x-ray backscatter detectors 830. Boom 832 allows beam stop 834 to intercept beam 828 as it emerges from the distal side of the scanned cargo container. Beam stop 834 is also referred to as a "beam catcher." In addition or alternatively to beam stop 834, an x-ray transmission detector may be mounted in opposition to beam 828. It is to be understood that the positions of the source 840 and the transmission detector 34 may be reversed, and that source 840 may be carried on the side of the cargo container that is distal to truck 824. It is, furthermore, to be understood that the term 'source' as used herein and in any appended claims, and as designated by numeral 840 in the drawings, refers to the entirety of the apparatus (designated by numeral 12 in FIG. 1) used to generate beam 828, and may have internal components that include, without limitation, apertures, choppers, collimators, etc.

The described embodiments of the invention are intended to be merely exemplary and numerous variations and modifications will be apparent to those skilled in the art. All such variations and modifications are intended to be within the scope of the present invention as defined in the appended claims.

We claim:

1. A method for creating an x-ray image of an object under inspection and detecting clandestine nuclear material associated with the object under inspection, the method comprising:

a. illuminating the object under inspection with penetrating radiation;
    b. detecting emission, including penetrating radiation, emanating from the object that is due solely to emission by the object under inspection and that has nothing to do with emission by any source other than the object under inspection;
    c. producing an x-ray image of the object based on the detected emission; and
    d. distinguishing between detected emission due to penetrating radiation scattered by the object and detected emission due to the clandestine nuclear material that is independent of whether the clandestine nuclear material is illuminated with penetrating radiation.

2. A method according to claim 1, wherein distinguishing includes distinguishing detected emission due to fissile material.

3. A method according to claim 1, wherein distinguishing includes distinguishing on the basis of x-rays emitted by the object.

4. A method according to claim 1, wherein distinguishing includes distinguishing on the basis of at least one of gamma rays and neutrons emitted by the object.

5. A method according to claim 1, wherein distinguishing includes distinguishing detected emission due to a dirty bomb.

6. A method according to claim 1, wherein illuminating the object includes illuminating the object intermittently, and distinguishing includes distinguishing based on at least the source- and detected-signal timing.

7. A method according to claim 1, wherein distinguishing includes distinguishing on the basis of gamma rays emitted by the object.

\* \* \* \* \*